(12) United States Patent
Wang et al.

(10) Patent No.: US 11,353,527 B2
(45) Date of Patent: Jun. 7, 2022

(54) SYSTEMS AND METHODS FOR WAVEFORM DETERMINATION IN MAGNETIC RESONANCE IMAGING

(71) Applicant: SHANGHAI UNITED IMAGING HEALTHCARE CO., LTD., Shanghai (CN)

(72) Inventors: Chaohong Wang, Shanghai (CN); Guobin Li, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1 day.

(21) Appl. No.: 16/919,119

(22) Filed: Jul. 2, 2020

(65) Prior Publication Data
US 2021/0018578 A1 Jan. 21, 2021

(30) Foreign Application Priority Data

Jul. 19, 2019 (CN) .......................... 201910653949.4
Nov. 26, 2019 (CN) .......................... 201911176210.5

(51) Int. Cl.
*G01V 3/00* (2006.01)
*G01R 33/28* (2006.01)
*G01R 33/567* (2006.01)
*G01R 33/54* (2006.01)
*A61B 5/055* (2006.01)

(52) U.S. Cl.
CPC ......... *G01R 33/288* (2013.01); *G01R 33/543* (2013.01); *G01R 33/5673* (2013.01); *A61B 5/055* (2013.01)

(58) Field of Classification Search
CPC .............. G01R 33/543; G01R 33/5659; G01R 33/3415; G01R 33/36; A61B 5/055

USPC .......................................................... 324/309
See application file for complete search history.

(56) References Cited

U.S. PATENT DOCUMENTS

| 6,236,204 | B1 | 5/2001 | Heid | |
|---|---|---|---|---|
| 2007/0015991 | A1* | 1/2007 | Fu | ........................ A61N 5/1049 600/407 |
| 2008/0036755 | A1* | 2/2008 | Bae | ........................ G06T 17/20 345/418 |

(Continued)

FOREIGN PATENT DOCUMENTS

| CN | 102288929 A | 12/2011 |
|---|---|---|
| CN | 107479015 A | 12/2017 |

(Continued)

OTHER PUBLICATIONS

Jürgen Hennig et al., High-Field MR Imaging, Springer, 48-52, 2011.
Ulrich Katscher et al., Transmit SENSE, Magnetic Resonance in Medicine, 49: 144-150, 2003.
Ulrich Katscher et al., Theoretical and Numerical Aspects of Transmit SENSE, IEEE Transactions on Medical Imaging, 23(4): 520-525, 2004.

(Continued)

*Primary Examiner* — Walter L Lindsay, Jr.
*Assistant Examiner* — Frederick Wenderoth
(74) *Attorney, Agent, or Firm* — Metis IP LLC

(57) ABSTRACT

The present disclosure provides systems and methods for magnetic resonance imaging. The method may include obtaining a pulse sequence for scanning an object, obtaining a tolerance parameter associated with the pulse sequence, determining, based on the pulse sequence and the tolerance parameter, a target waveform for scanning the object, and causing an MRI device to scan the object based on the target waveform.

20 Claims, 13 Drawing Sheets

(56) References Cited

U.S. PATENT DOCUMENTS

| | | | |
|---|---|---|---|
| 2009/0241006 A1* | 9/2009 | Liikanen | H03M 13/253 |
| | | | 714/752 |
| 2012/0116149 A1* | 5/2012 | Pilla | A61N 2/006 |
| | | | 600/14 |
| 2014/0084918 A1 | 3/2014 | Kurokawa | |
| 2014/0232393 A1 | 8/2014 | Wheaton et al. | |
| 2015/0115956 A1 | 4/2015 | Ackerman et al. | |
| 2015/0241535 A1 | 8/2015 | Grodzki | |
| 2015/0346300 A1* | 12/2015 | Setsompop | G01R 33/4828 |
| | | | 324/309 |
| 2015/0369891 A1* | 12/2015 | Miyazaki | G01R 33/5617 |
| | | | 324/309 |
| 2015/0369897 A1 | 12/2015 | Keil | |
| 2017/0003362 A1 | 1/2017 | Kuratani | |
| 2017/0135854 A1* | 5/2017 | Rogers | A61F 7/007 |
| 2017/0192068 A1* | 7/2017 | Taniguchi | G01R 33/3854 |
| 2017/0356973 A1 | 12/2017 | Wheaton | |
| 2018/0376441 A1 | 12/2018 | Reykowski et al. | |
| 2019/0120920 A1 | 4/2019 | Harder et al. | |
| 2019/0195977 A1 | 6/2019 | De Oliveira et al. | |
| 2021/0109180 A1 | 4/2021 | Boernert et al. | |

FOREIGN PATENT DOCUMENTS

| | | |
|---|---|---|
| CN | 105931242 B | 5/2018 |
| CN | 108186015 A | 6/2018 |
| CN | 109009111 A | 12/2018 |
| JP | 2014022453 A | 2/2014 |

OTHER PUBLICATIONS

Kay Nehrke et al. On the Performance and Accuracy of 2D Navigator Pulses, Magnetic Resonance Imaging, 17(8): 1173-1161, 1999.

First Office Action in Chinese Application No. 201910653949.4 dated Mar. 18, 2021, 19 pages.

Christiane Katharina Kuhl et al. Do T2-Weighted Pulsel Sequences Help with the Differential Diagnosis of Enhancing Lesions in Dynamic Breast MRI?, Journal of Magnetic Resonance Imaging, 9: 187-196, 1999.

Lu, Minjie et al., Optimal MR Protocol and Sequences Selection for Aortic Disease, Compilation of Papers of the 13th National Radiology Conference of the Chinese Medical Association CT (vol. 2), 2006, 21 pages.

* cited by examiner

SYSTEMS AND METHODS FOR WAVEFORM DETERMINATION IN MAGNETIC RESONANCE IMAGING

CROSS-REFERENCE TO RELATED APPLICATIONS

This application claims priority of Chinese Patent Application No. 201910653949.4, filed on Jul. 19, 2019, and Chinese Patent Application No. 201911176210.5, filed on Nov. 26, 2019, the entire contents of each of which are hereby incorporated by reference.

TECHNICAL FIELD

The disclosure generally relates to magnetic resonance imaging (MRI), and more particularly, relates to systems and methods for determining a waveform in MRI.

BACKGROUND

Magnetic resonance imaging (MRI) device is a noninvasive medical imaging technique, which is widely used for clinical diagnosis. In an MRI process, an MRI device may detect a plurality of echo signals by applying a pulse sequence on a subject (e.g., a patient). The pulse sequence may include a series of radiofrequency (RF) pulses and gradient pulses. Generally, a processing device of the MRI device may need to determine waveforms corresponding to the pulse sequence, and then transmit them to a driving unit for execution. However, a pulse sequence for a clinical application may include thousands of gradient pulses. The waveform determination process may be complicated and time-consuming, resulting in a relatively long scanning time. Additionally, different subjects may have different practical needs. A unified scanning strategy (e.g., using a same gradient pulse sequence to scan an adult and a child) may cause a poor user experience to the user. Therefore, it is desirable to provide systems and methods for reducing the scanning time and providing personalized scanning strategies to improve the user experience of the MRI device.

SUMMARY

According to a first aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a pulse sequence for scanning an object. The system may obtain a tolerance parameter associated with the pulse sequence. The system may determine, based on the pulse sequence and the tolerance parameter, a target waveform for scanning the object. The system may cause an MRI device to scan the object based on the target waveform.

In some embodiments, the pulse sequence may include at least one of a radiofrequency (RF) pulse sequence or a gradient pulse sequence.

In some embodiments, to determine, based on the pulse sequence and the tolerance parameter, a target waveform for scanning the object, the system may determine the target waveform based on a relationship among the pulse sequence, the tolerance parameter, and the target waveform.

In some embodiments, to determine, based on the pulse sequence and the tolerance parameter, a target waveform for scanning the object, the system may query a waveform database based on the pulse sequence and the tolerance parameter. The system may determine the target waveform based on a query result.

In some embodiments, to determine, based on the pulse sequence and the tolerance parameter, a target waveform for scanning the object, the system may determine, based on the pulse sequence, an initial waveform. The system may determine the target waveform by adjusting, based on the tolerance parameter, the initial waveform.

In some embodiments, to determine, based on the pulse sequence, an initial waveform, the system may determine the initial waveform based on a relationship between the pulse sequence and the initial waveform.

In some embodiments, to determine, based on the pulse sequence, an initial waveform, the system may obtain one or more first features of the pulse sequence, the one or more first features corresponding to the initial waveform. The system may obtain one or more second features of each of multiple candidate reference sequences from a waveform library. The one or more second features of the each candidate reference sequence may correspond to a candidate reference waveform. The system may determine, based on the one or more first features and the one or more second features, a matching degree between the pulse sequence and each of the multiple candidate reference sequences. The system may determine, based on the matching degree, the initial waveform.

In some embodiments, to determine, based on the matching degree, the initial waveform, the system may identify a highest matching degree among the matching degrees between the pulse sequence and the multiple candidate reference sequences. The system may determine, based on a reference waveform corresponding to the reference sequence of the highest matching degree, the initial waveform.

In some embodiments, to adjust, based on the tolerance parameter, the initial waveform, the system may adjust one or more waveform parameters of the initial waveform based on the tolerance parameter. The one or more waveform parameters of the initial waveform may include at least one of a pulse amplitude, a pulse phase, a slope, or a profile of the initial waveform.

In some embodiments, the tolerance parameter may include an acoustic noise expectation corresponding to the gradient pulse sequence, the system may determine a scanning time for scanning the object based on the target waveform. The system may determine whether the scanning time satisfies a compliance condition. In response to determining that the scanning time fails to satisfy the compliance condition, the system may adjust the acoustic noise expectation corresponding to the gradient pulse sequence.

In some embodiments, the tolerance parameter may include a scanning time corresponding to the gradient pulse sequence, the system may determine an acoustic noise expectation corresponding to the gradient pulse sequence based on the target waveform. The system may determine whether the acoustic noise expectation corresponding to the gradient pulse sequence satisfies a compliance condition. In response to determining that the acoustic noise expectation corresponding to the gradient pulse sequence fails to satisfy the compliance condition, the system may adjust the scanning time corresponding to the gradient pulse sequence.

In some embodiments, the target waveform may include at least one gradient waveform. To cause the MRI device to scan the object based on the target waveform, the system may initiate a gradient channel of the MRI device corresponding to the at least one gradient waveform. The gradient channel may include at least one of an X-axis gradient channel, a Y-axis gradient channel, or a Z-axis gradient channel. The system may transmit the at least one gradient waveform using the corresponding gradient channel.

In some embodiments, the tolerance parameter may include a specific absorption rate (SAR) corresponding to the RF pulse sequence. The system may determine whether the scanning time satisfies a compliance condition. In response to determining that the scanning time fails to satisfy the compliance condition, the system may adjust the SAR.

In some embodiments, the tolerance parameter may include a scanning time corresponding to the RF pulse sequence. The system may determine a specific absorption rate (SAR) corresponding to the RF pulse sequence based on the target waveform. The system may determine whether the SAR corresponding to the RF pulse sequence satisfies a compliance condition. In response to determining that the SAR corresponding to the RF pulse sequence fails to satisfy the compliance condition, the system may adjust the scanning time corresponding to the RF pulse sequence.

In some embodiments, the target waveform may include at least one RF pulse waveform. The system may perform a pulse frequency modulation on the at least one RF pulse waveform. The system may initiate an RF transmission channel of the MRI device corresponding to the at least one RF pulse waveform. The system may transmit the at least one RF pulse waveform using the corresponding RF transmission channel simultaneously.

In some embodiments, the system may obtain an MRI signal of the object based on the target waveform. The system may generate an image of the object by reconstructing the MRI signal. The system may determine whether the image meets a quality threshold. In response to determining that the image does not meet the quality threshold, the system may adjust the tolerance parameter.

According to a second aspect of the present disclosure, a method is provided. The method may be implemented on at least one computing device, each of which may include at least one processor and a storage device. The method may include obtaining a pulse sequence for scanning an object; obtaining a tolerance parameter associated with the pulse sequence; determining, based on the pulse sequence and the tolerance parameter, a target waveform for scanning the object; and causing an MRI device to scan the object based on the target waveform.

According to a third aspect of the present disclosure, a magnetic resonance (MR) apparatus is provided. The MR apparatus may include an MR scanner including a gradient coil system, a user interface, a processing device, and a control device. The user interface may be configured to enable a user to input a tolerance parameter associated with a pulse sequence The processing device may be configured to determine, based on the pulse sequence and the tolerance parameter, a target waveform. The control device may be configured to cause the MR scanner to scan an object according to the target waveform. A gradient field corresponding to the target waveform may be produced in the MR scanner by the gradient coil system of the MR scanner.

According to a fourth aspect of the present disclosure, a system is provided. The system may include at least one storage device storing executable instructions, and at least one processor in communication with the at least one storage device. When executing the executable instructions, the at least one processor may cause the system to perform one or more of the following operations. The system may obtain a pulse sequence for scanning an object, wherein the pulse sequence includes one or more first features corresponding to an initial waveform. The system may obtain multiple candidate reference sequences, wherein each of the multiple candidate reference sequences includes one or more second features. For each of the multiple candidate reference sequences, the system may determine, based on the one or more first features and the one or more second features, a matching degree between the pulse sequence and the each candidate reference sequence. The system may determine, based on the matching degrees, a target waveform. The system may cause an MRI device to scan the object based on the target waveform.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1A:
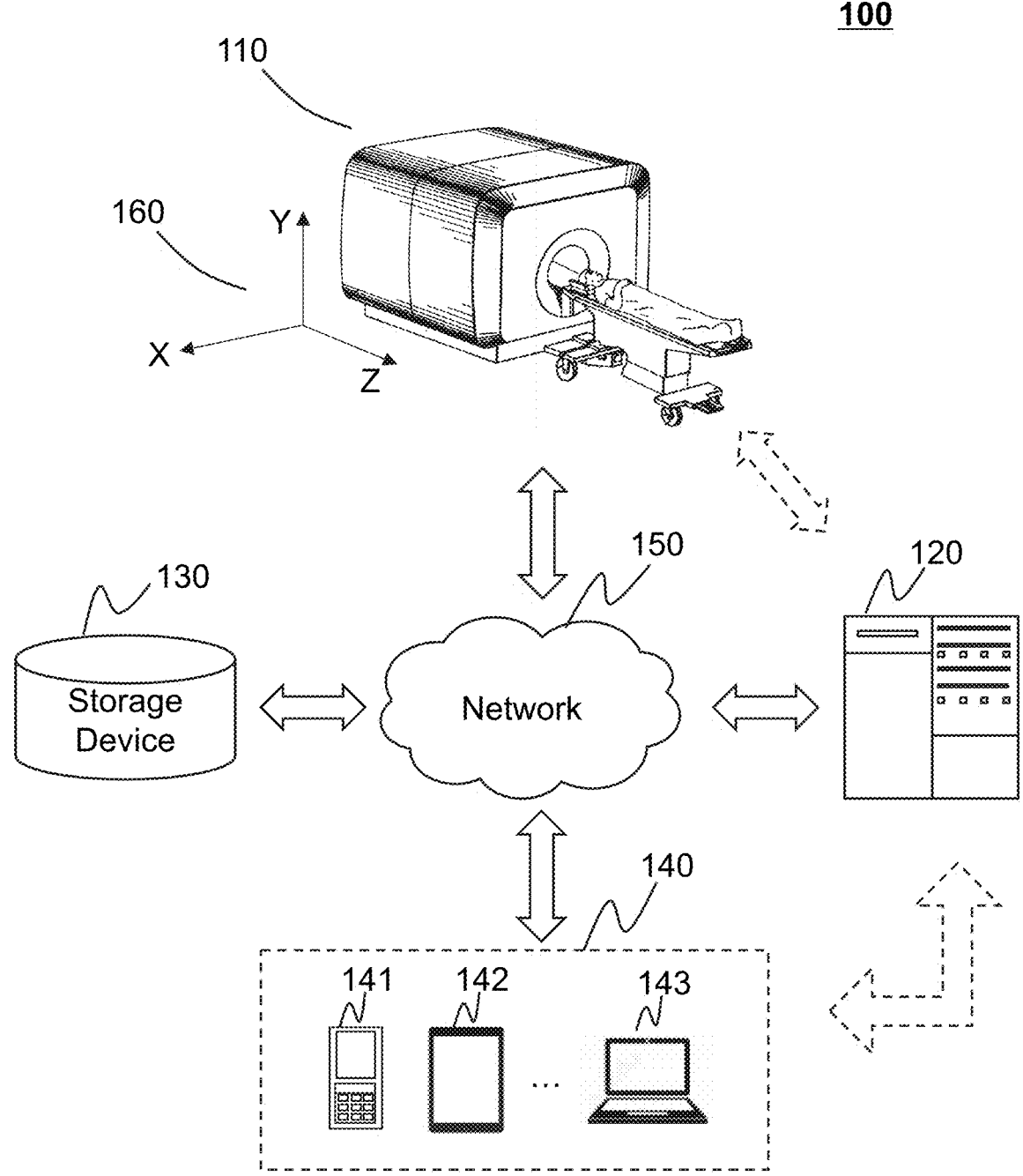
FIG. 1A is a schematic diagram illustrating an exemplary MRI system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for providing personalized scanning strategies of an MRI device. The system may obtain a pulse sequence for scanning an object. The system may obtain a tolerance parameter associated with the pulse sequence. The system may determine a target waveform for scanning the object based on the pulse sequence and the tolerance parameter. The system may cause the MRI device to scan the object based on the target waveform. According to the systems and/or methods disclosed herein, a user may set the tolerance parameter according to practical needs, thereby promoting user interaction between the user and the MRI device and improving the user experience. For example, when the object is a child who cannot tolerate loud noise, the tolerance parameter may include an acoustic noise expectation. The system may cause the MRI device to scan the child with a waveform determined based on a specific noise expectation inputted by a user (e.g., a doctor). As another example, when the object is a patient with an implant in the body, the tolerance parameter may include a specific absorption rate (SAR). The system may cause the MRI device to scan the patient with a waveform determined based on a specific SAR inputted by a user.

Another aspect of the present disclosure relates to systems and methods for determining a target waveform of a pulse sequence for scanning an object. The system may obtain a pulse sequence for scanning the object, wherein the pulse sequence includes one or more first features. The system may obtain multiple candidate reference sequences. Each of the multiple candidate reference sequences may include one or more second features corresponding to a candidate reference waveform. The system may determine a matching degree between the pulse sequence and each of multiple candidate reference sequences based on the one or more first features and the one or more second features. The system may determine the target waveform of the pulse sequence based on the matching degree. According to the systems and/or methods disclosed herein, the target waveform may be obtained by querying a storage device storing the multiple candidate reference sequences, instead of directly determining the target waveform in real time, based on the pulse sequence during an MRI process, thereby reducing the scanning time and improving the user experience.

FIG. 1A is a schematic diagram illustrating an exemplary MRI system according to some embodiments of the present disclosure. As shown in FIG. 1, the MRI system 100 may include an MRI device 110, a processing device 120, a storage device 130, one or more terminal devices 140, and a network 150.

The MRI device 110 may be configured to acquire imaging data relating to at least one part of a subject. The MRI device 110 may scan the subject or a portion thereof that is located within its detection region and generate MR image data relating to the subject or the portion thereof. For example, the MRI device 110 may detect a plurality of echo signals by applying an MR pulse sequence on the subject. In some embodiments, the MRI device 110 may include, for example, a main magnet, a gradient coil (or also referred to a spatial encoding coil), a radio frequency (RF) coil, etc., as described in connection with FIG. 1B. In some embodiments, the MRI device 110 may be a permanent magnet MRI device, a superconducting electromagnet MRI device, or a resistive electromagnet MRI device, etc., according to types of the main magnet. In some embodiments, the MRI device 110 may be a high-field MRI device, a mid-field MRI device, and a low-field MRI device, etc., according to the intensity of the magnetic field. In some embodiments, the MRI device 110 may be a close-bore device or an open-bore device.

The subject may be biological or non-biological. For example, the subject may include a patient, a man-made object, etc. As another example, the subject may include a specific portion, organ, and/or tissue of the patient. For example, the subject may include the head, the neck, the thorax, the heart, the stomach, a blood vessel, soft tissue, a tumor, nodules, or the like, or any combination thereof.

For illustration purposes, a reference coordinate system 160 including an X-axis, a Y-axis, and a Z-axis may be established as illustrated in FIG. 1A. The reference coordinate system 160 may relate to MR scanning, data acquisition, image reconstruction, etc. In some embodiments, the longitudinal direction of the table of the MRI device 110 may be defined as a Z-direction (i.e., the Z-axis illustrated in FIG. 1A). The horizontal direction of the table may be defined as an X-direction (i.e., the X-axis illustrated in FIG. 1A). A direction that is perpendicular to an X-Z plane (also referred to as a coronal plane of an imaging subject) may be defined as a Y-direction (i.e., the Y-axis illustrated in FIG. 1A).

In some embodiments, the MRI device 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. It should be noted that the slice-selection direction, the phase-encoding direction, and the frequency-encoding direction may be modified according to actual needs, and the modification may do not depart the scope of the present disclosure. More description of the MRI device 110 may be found elsewhere in the present disclosure. See, e.g., FIG. 2 and the description thereof.

The processing device 120 may process data and/or information obtained from the MRI device 110, the terminal device(s) 140, and/or the storage device 130. For example, according to a pulse sequence for scanning an object, the processing device 120 may determine an initial waveform corresponding to the pulse sequence from a waveform library, thereby reducing a time to determine the initial waveform based on the pulse sequence. As another example, according to a tolerance parameter inputted by a user, the processing device 120 may adjust the initial waveform corresponding to the pulse sequence to obtain a target waveform, thereby promoting the user interaction between the user and the MRI device 110 and improving the user experience. The processing device 120 may be a central processing unit (CPU), a digital signal processor (DSP), a system on a chip (SoC), a microcontroller unit (MCU), or the like, or any combination thereof. In some embodiments, the processing device 120 may be a computer, a user console, a single server or a server group, etc. The server group may be centralized or distributed. In some embodiments, the processing device 120 may be local or remote. For example, the processing device 120 may access information and/or data stored in or acquired by the MRI device 110, the terminal device(s) 140, and/or the storage device 130 via the network 150. As another example, the processing device 120 may be directly connected to the MRI device 110, the terminal device(s) 140, and/or the storage device 130 to access stored or acquired information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device 200 having one or more components as described in FIG. 3 in the present disclosure.

The storage device 130 may store data, instructions, and/or any other information. In some embodiments, the storage device 130 may store data obtained from the MRI device 110, the terminal device(s) 140, and/or the processing device 120. For example, the storage device 130 may store multiple candidate reference waveforms designated by a user (e.g., a doctor, an imaging technician). In some embodiments, the storage device 130 may store data and/or instructions that the processing device 120 may execute or use to perform exemplary methods/systems described in the present disclosure. For example, the storage device 130 may store instructions that the processing device 120 may execute to determine a target waveform for scanning an object. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components (e.g., the processing device 120, the terminal device(s) 140, etc.) in the MRI system 100. One or more components in the MRI system 100 may access the data or instructions stored in the storage device 130 via the network 150. In some embodiments, the storage device 130 may be directly connected to or communicate with one or more other components (e.g., the processing device 120, the terminal device(s) 140, etc.) in the MRI system 100. In some embodiments, the storage device 130 may be part of the processing device 120.

The terminal device(s) 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal device(s) 140 may remotely operate the MRI device 110 and/or the processing device 120. In some embodiments, the terminal device(s) 140 may operate the MRI device 110 and/or the processing device 120 via a wireless connection. In some embodiments, the terminal device(s) 140 may receive information and/or instructions inputted by a user, and send the received information and/or instructions to the MRI device 110 or to the processing device 120 via the network 150. In some embodiments, the terminal device(s) 140 may receive data and/or information from the processing device 120. In some embodiments, the terminal device(s) 140 may be part of the processing device 120. In some embodiments, the terminal device(s) 140 may be omitted.

The network 150 may include any suitable network that can facilitate the exchange of information and/or data for the MRI system 100. In some embodiments, one or more components (e.g., the MRI device 110, the processing device 120, the storage device 130, the terminal device(s) 140, etc.) of the MRI system 100 may communicate information and/or data with one or more other components of the MRI system 100 via the network 150. For example, the processing device 120 may obtain data from the MRI device 110 via the network 150. As another example, the processing device 120 may obtain user instructions from the terminal device(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points, such as base stations and/or internet exchange points, through which one or more components of the MRI system 100 may be connected to the network 150 to exchange data and/or information.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. In some embodiments, the MRI system 100 may further include one or more additional components, and/or one or more components of the MRI system 100 may be omitted. For example, the MRI system 100 may further include one or more power supplies (not shown in FIG. 1) connected to one or more components of the MRI system 100 (e.g., the MRI device 110, the processing device 120, the storage device 130, the terminal device(s) 140, etc.).

Figure 1B:
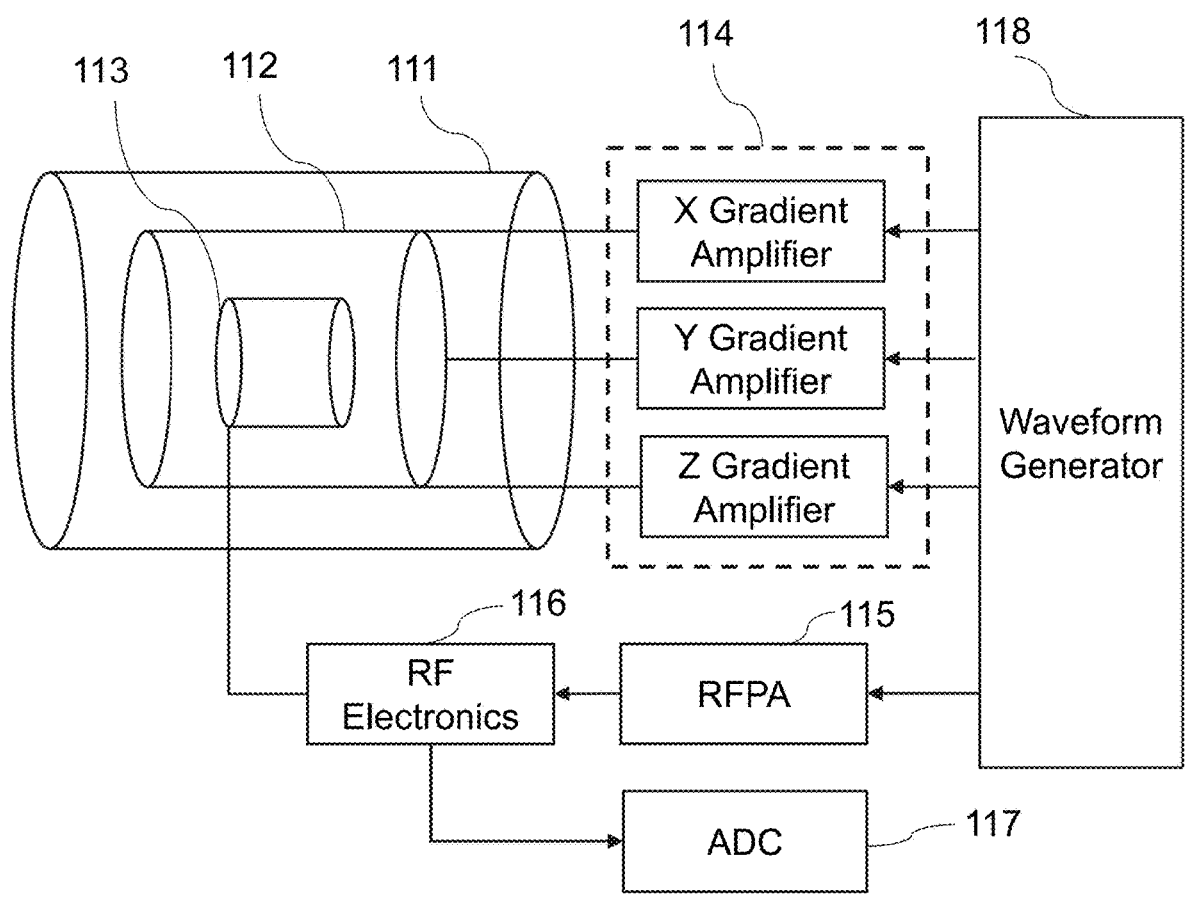
FIG. 1B is a schematic diagram illustrating an exemplary MRI device according to some embodiments of the present disclosure.
Figure 2:
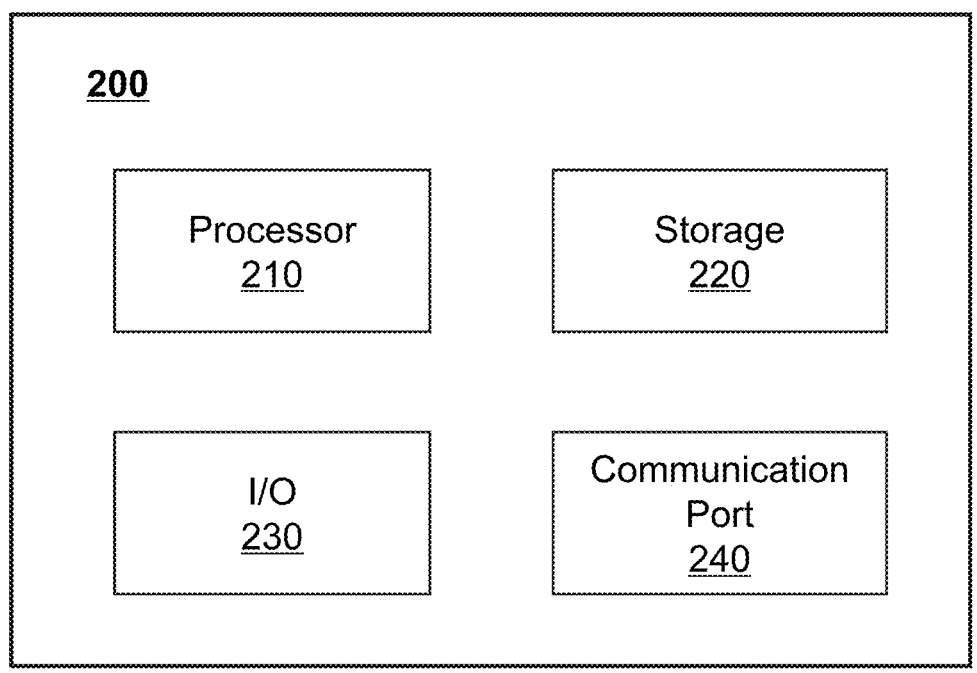
FIG. 2 is a schematic diagram illustrating hardware and/or software components of an exemplary computing device on which the processing device may be implemented according to some embodiments of the present disclosure.

FIG. 1B is a schematic diagram illustrating an exemplary MRI device according to some embodiments of the present disclosure. One or more components of the MRI device 110 are illustrated in FIG. 2. As illustrated, the main magnet 111 may generate a first magnetic field (or referred to as a main magnetic field) that may be applied to an object (also referred to as a subject) exposed inside the field. The main magnet 111 may include a resistive magnet or a superconductive magnet that both need a power supply (not shown) for operation. Alternatively, the main magnet 111 may include a permanent magnet. The main magnet 111 may also control the homogeneity of the generated main magnetic field. Some shim coils may be in the main magnet 111. The shim coils placed in the gap of the main magnet 111 may compensate for the inhomogeneity of the magnetic field of the main magnet 111.

Gradient coils 112 may be located inside the main magnet 111. The gradient coils 112 may generate a second magnetic field (or referred to as a gradient magnetic field or a gradient field) The gradient field may be superimposed on the main field (or main magnetic field) generated by the main magnet 111 and distort the main field so that the magnetic orientations of the protons of an object may vary as a function of their positions inside the gradient field, thereby encoding spatial information into MR signals generated by a region of the object being imaged. The gradient coils 112 may include X coils (e.g., configured to generate a gradient field Gx corresponding to the X direction), Y coils (e.g., configured to generate a gradient field Gy corresponding to the Y direction), and/or Z coils (e.g., configured to generate a gradient field Gz corresponding to the Z direction) (not shown in FIG. 1B). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 112 may allow spatial encoding of MR signals for image reconstruction. During an MRI scanning process, the gradient fields generated by the gradient coils 112 may be rapidly switched in the main field of the MRI device to continuously perform spatial and/or spectral information encoding during which the gradient coils 112 may generate strong acoustic noises. In some embodiments, the acoustic noises may be reduced by improving the design of the gradient coils 112 (e.g., by using gradient coils that have been evacuated). Alternatively, the acoustic noises may be reduced by improving the way the gradient fields of a pulse sequence is used. More descriptions about the way the gradient fields of a pulse sequence is used may be found elsewhere in the present disclosure (e.g., FIGS. 9A to 9C, and the descriptions thereof).

The gradient coils 112 may be connected with one or more gradient amplifiers 114. The one or more gradient amplifiers 114 may include an X gradient amplifier, a Y gradient amplifier, a Z gradient amplifier, or the like, or any combination thereof. The one or more amplifiers 114 may be connected to a waveform generator 118. The waveform generator 118 may generate gradient waveforms that are applied to the one or more gradient amplifiers 114 based on one or more gradient pulses of a gradient pulse sequence. A gradient amplifier may amplify a waveform. An amplified waveform may be applied to one of the gradient coils 112 to generate a gradient field in the X-axis, the Y-axis, or the Z-axis. The gradient coils 112 may be designed for either a close-bore MRI device or an open-bore MRI device. In some instances, all three sets of coils of the gradient coils 112 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 1B may be the same as or similar to those described in FIG. 1A.

In some embodiments, radio frequency (RF) coils 113 may be located inside the main magnet 111 and serve as transmitters (i.e., the corresponding RF coils are served as RF emitting coils), receivers (i.e., the corresponding RF coils are served as RF receiving coils), or both. The RF coils 113 may be in connection with RF electronics 116 that may be configured or used as one or more integrated circuits (ICs) functioning as a waveform transmitter and/or a waveform receiver. The RF electronics 116 may be connected to a radiofrequency power amplifier (RFPA) 115 and an analog-to-digital converter (ADC) 117.

When used as transmitters, the RF coils 113 may generate RF signals that provide a third magnetic field that is utilized to generate MR signals related to the region of the object being imaged. The third magnetic field may be perpendicular to the main field. The waveform generator 118 may generate an RF pulse waveform based on an RF pulse of an RF pulse sequence. The RF pulse may be amplified by the RFPA 115, processed by the RF electronics 116, and applied to the RF coils 113 to generate the RF signals in response to a powerful current generated by the RF electronics 116 based on the amplified RF pulse waveform. In some embodiments, the RF coils 113 may include multiple sets of RF emitting coils each of which corresponds to one RFPA 115. That is, each set of RF emitting coils may correspond to an RF transmission channel. An RF pulse waveform (e.g., the phase, the amplitude, etc.) corresponding to an RF transmission channel may be independently controlled by a controller. In some embodiments, when an RF pulse sequence corresponds to a plurality of RF pulse waveforms, the processing device 120 may initiate a plurality of sets of RF emitting coils each of which corresponds to one RF pulse waveform. The processing device 120 may apply each RF pulse waveform to the corresponding RF emitting coils set to drive the plurality of sets of RF emitting coils to simultaneously emit RF signals for scanning the subject.

When used as receivers, the RF coils 113 may be responsible for detecting MR signals (e.g., echoes). After excitation, the MR signals generated by the object may be sensed by the RF coils 113. The receive amplifier then may receive the sensed MR signals from the RF coils 113, amplify the sensed MR signals, and provide the amplified MR signals to the ADC 117. The ADC 117 may transform the MR signals from analog signals to digital signals. The digital MR signals then may be sent to the processing device 120 for sampling.

In some embodiments, the gradient coils 112 and the RF coils 113 may be circumferentially positioned with respect to the object. It is understood by those skilled in the art that the main magnet 111, the gradient coils 112, and the RF coils 113 may be situated in a variety of configurations around the object.

It should be noted that the processing device 120 may trigger the various coils (e.g., RF transmitting coils, RF receiving coils, and/or gradient coils) to receive the MR signals and/or emit the corresponding pulse signals. That is, the processing device 120 may cause the RF coils 113 and/or the gradient coils 112 to produce corresponding signals based on the corresponding waveform.

In some embodiments, the RFPA 115 may amplify an RF pulse (e.g., the power of the RF pulse, the voltage of the RF pulse) such that an amplified RF pulse is generated to drive the RF coils 113. The RFPA 115 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 115 may include a linear RFPA or a nonlinear RFPA. In some embodiments, the RFPA 115 may include one or more RFPAs.

It should be noted that the above description of the MRI device 110 is merely provided for the purposes of illustration, and not intended to limit the scope of the present disclosure. For persons having ordinary skills in the art, multiple variations and modifications may be made under the teachings of the present disclosure. For example, the MRI device 110 may further include an object positioning system (not shown). The object positioning system may include an object cradle and a transport device. The object may be placed on the object cradle and be positioned by the transport device within the bore of the main magnet 111.

FIG. 2 is a schematic diagram illustrating hardware and/or software components of an exemplary computing device on which the processing device may be implemented according to some embodiments of the present disclosure. The computing device 200 may be used to implement any component of the MRI system 100 as described herein. For example, the processing device 120 and/or a terminal device may be implemented on the computing device 200, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal device(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operations A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the MRI device 110, the terminal device(s) 140, the storage device 130, or any other component of the MRI system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program that, when executed by the processing device 120, may cause the processing device 120 to determine a target waveform corresponding to an excitation radio frequency (RF) pulse to excite one or more slices of an object in conjunction with a slice selection gradient in an excitation in an MRI scan.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the MRI device 110, the terminal device(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
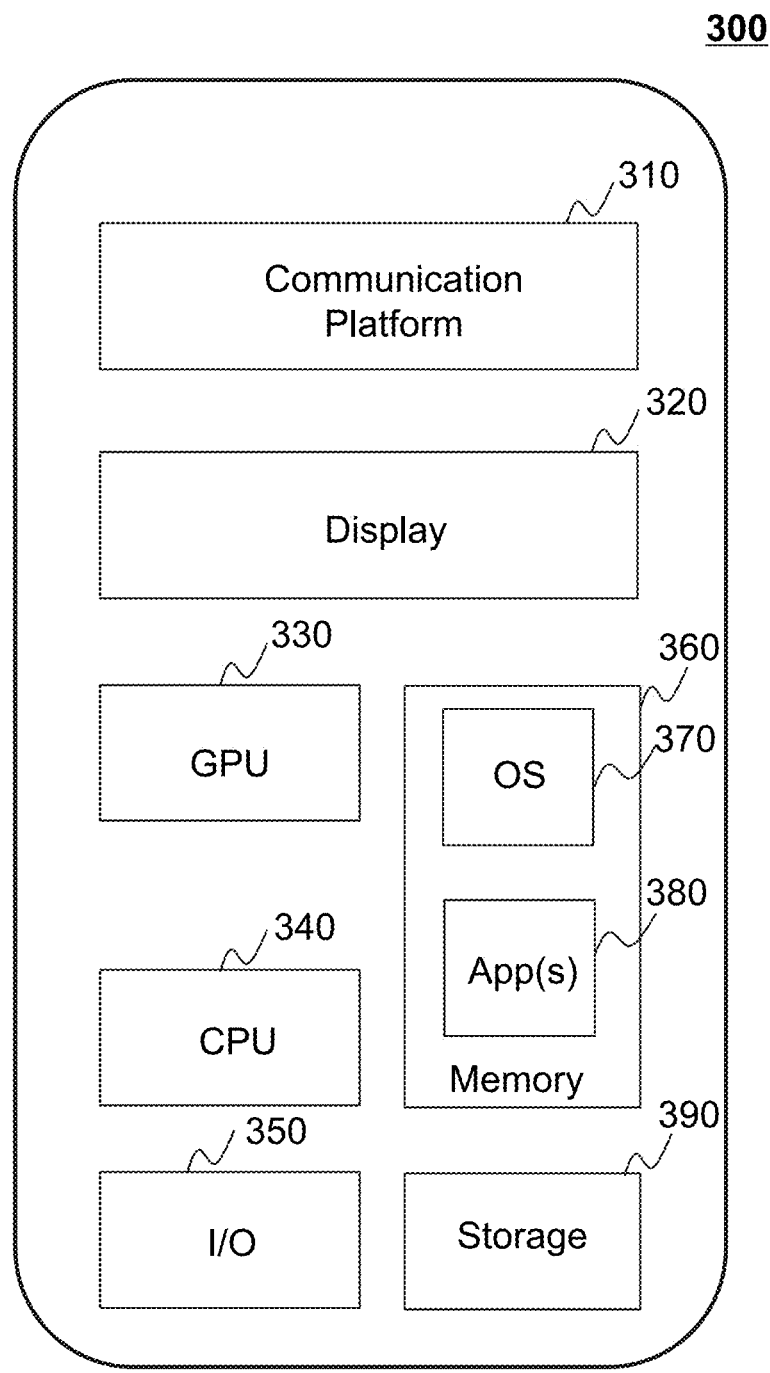
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device according to some embodiments of the present disclosure. In some embodiments, one or more components (e.g., the terminal device(s) 140 and/or the processing device 120) of the MRI system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the MRI system via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
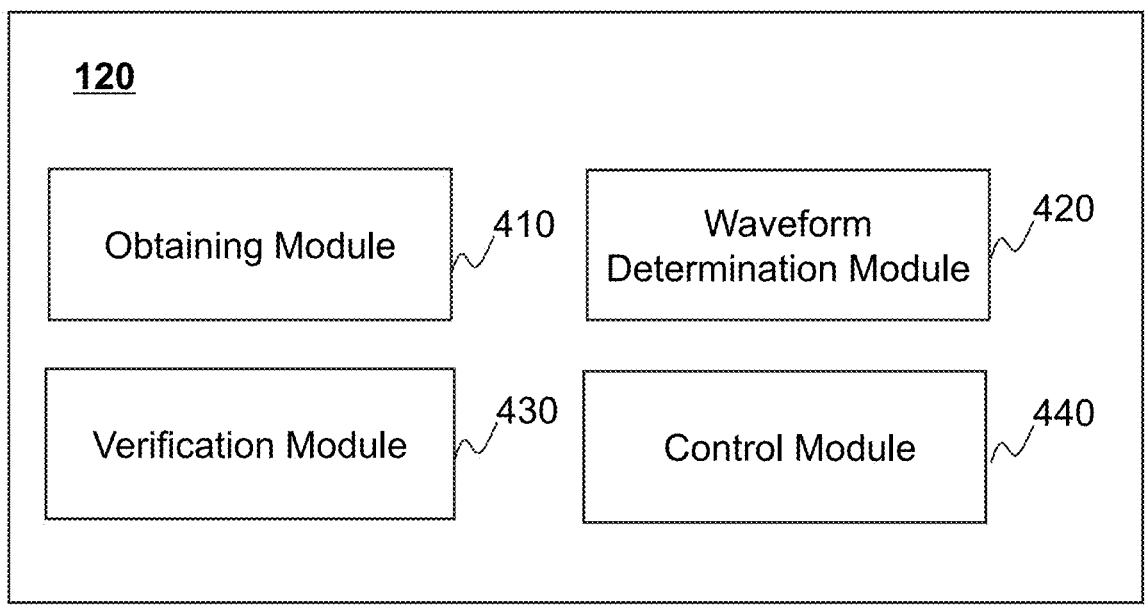
FIG. 4 is a block diagram illustrating exemplary processing device according to some embodiments of the present disclosure.

FIG. 4 is a block diagram illustrating exemplary processing device 120 according to some embodiments of the present disclosure. In some embodiments, the processing device 120 may be implemented on the computing device 200 (e.g., the processor 210) illustrated in FIG. 2 or a CPU 340 as illustrated in FIG. 3. As illustrated in FIG. 4, the processing device 120 may include an obtaining module 410, a waveform determination module 420, a verification module 430, and a control module 440. Each of the modules described above may be a hardware circuit that is designed to perform certain actions, e.g., according to a set of instructions stored in one or more storage media, and/or any combination of the hardware circuit and the one or more storage media.

The obtaining module 410 may be configured to obtain data and/or information for magnetic resonance imaging (MRI). For example, the obtaining module 410 may obtain a pulse sequence for scanning an object. The obtaining module 410 may obtain a tolerance parameter associated with the pulse sequence. As used herein, a tolerance parameter may be any parameter (and/or a value of such a parameter) that may affect the execution of a scan using an MRI device. For example, the tolerance parameter may be a scanning time, an acoustic noise expectation (e.g., expressed in decibel (dB)), a specific absorption rate (SAR, expressed in watts/Kg) or its distribution in the object, or the like. In some embodiments, the pulse sequence may include a radiofrequency (RF) pulse sequence, a gradient pulse sequence, or the like, or a combination thereof. Different pulse sequences may correspond to different tolerance parameters. For example, the acoustic noise expectation may be designated as the tolerance parameter with respect to a gradient pulse sequence since noises caused by the MRI device are mainly related to gradient coils of the MRI device. As another example, the SAR may be designated as the tolerance parameter with respect to an RF pulse sequence since the absorption of electromagnetic energies by the object is mainly related to RF signals emitted by RF emitting coils of the MRI device.

The waveform determination module 420 may be configured to determine a target waveform for scanning the object based on the pulse sequence and the tolerance parameter. The target waveform may be configured to enable the corresponding coils to produce corresponding pulse signals. In some embodiments, the waveform determination module 420 may determine the target waveform based on a relationship among the pulse sequence, the tolerance parameter, and the target waveform. In some embodiments, the waveform determination module 420 may query a waveform database based on the pulse sequence and the tolerance parameter to obtain the target waveform. In some embodiments, the waveform determination module 420 may determine an initial waveform corresponding to the pulse sequence. The waveform determination module 420 may determine the target waveform by adjusting the initial waveform based on the tolerance parameter.

The verification module 430 may be configured to determine a focus parameter based on the target waveform. The focus parameter may be a parameter correlating with the tolerance parameter. The verification module 430 may determine whether the focus parameter satisfies a compliance condition. In some embodiments, the compliance condition may be a threshold corresponding to the focus parameter. For example, if the tolerance parameter is the acoustic noise expectation, the focus parameter may be the scanning time. The compliance condition may be a scanning time threshold. In response to determining that the scanning time (i.e., the focus parameter) is greater than the scanning time threshold, the verification module 430 may determine that the focus parameter fails to satisfy the compliance condition. In response to determining that the scanning time is less than (or equal to) the scanning time threshold, the verification module 430 may determine that the focus parameter satisfies the compliance condition. In some embodiments, if the user accepts the focus parameter via, e.g., a terminal device, the verification module 430 may determine that the focus parameter satisfies the compliance condition. If the user does not accept the focus parameter via the terminal device, the verification module 430 may determine that the focus parameter does not satisfy the compliance condition.

The control module 440 may be configured to cause an MRI device to scan the object with the target waveform. The control module 440 may transmit the target waveform to a driving unit for executing the target waveform. In some embodiments, the target waveform may include one or more gradient waveforms. The control module 440 may initiate gradient channels of the MRI device corresponding to the one or more gradient waveforms. The gradient channel(s) may include an X-axis gradient channel (corresponding to the X-axis gradient coils), a Y-axis gradient channel (corresponding to the Y-axis gradient coils), or a Z-axis gradient channel (corresponding to the Z-axis gradient coils), or the like, or any combination thereof. The control module 440 may cause the corresponding gradient coils to transmit the gradient waveforms using the corresponding gradient channels. In some embodiments, the target waveform may include one or more RF pulse waveforms. The control module 440 may perform a pulse frequency modulation on at least one of the one or more RF pulse waveforms. The control module 440 may initiate RF transmission channels of the MRI device each of which corresponds to an RF pulse waveform. The control module 440 may transmit the modulated RF pulse waveforms using the corresponding RF transmission channels simultaneously. The control module 440 may cause RF coils corresponding to each transmission channel to emit RF signals corresponding to the RF pulse waveform. In some embodiments, the target waveform may include a gradient waveform and an RF pulse waveform.

The control module 440 may initiate the corresponding RF transmission channel and the corresponding gradient channel. The control module 440 may transmit the corresponding waveform using the corresponding transmission channels.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the waveform determination module 420 and the verification module 430 may be integrated into a single module. As another example, some other components/modules (e.g., a storage module) may be added into the processing device 120.

Figure 5:
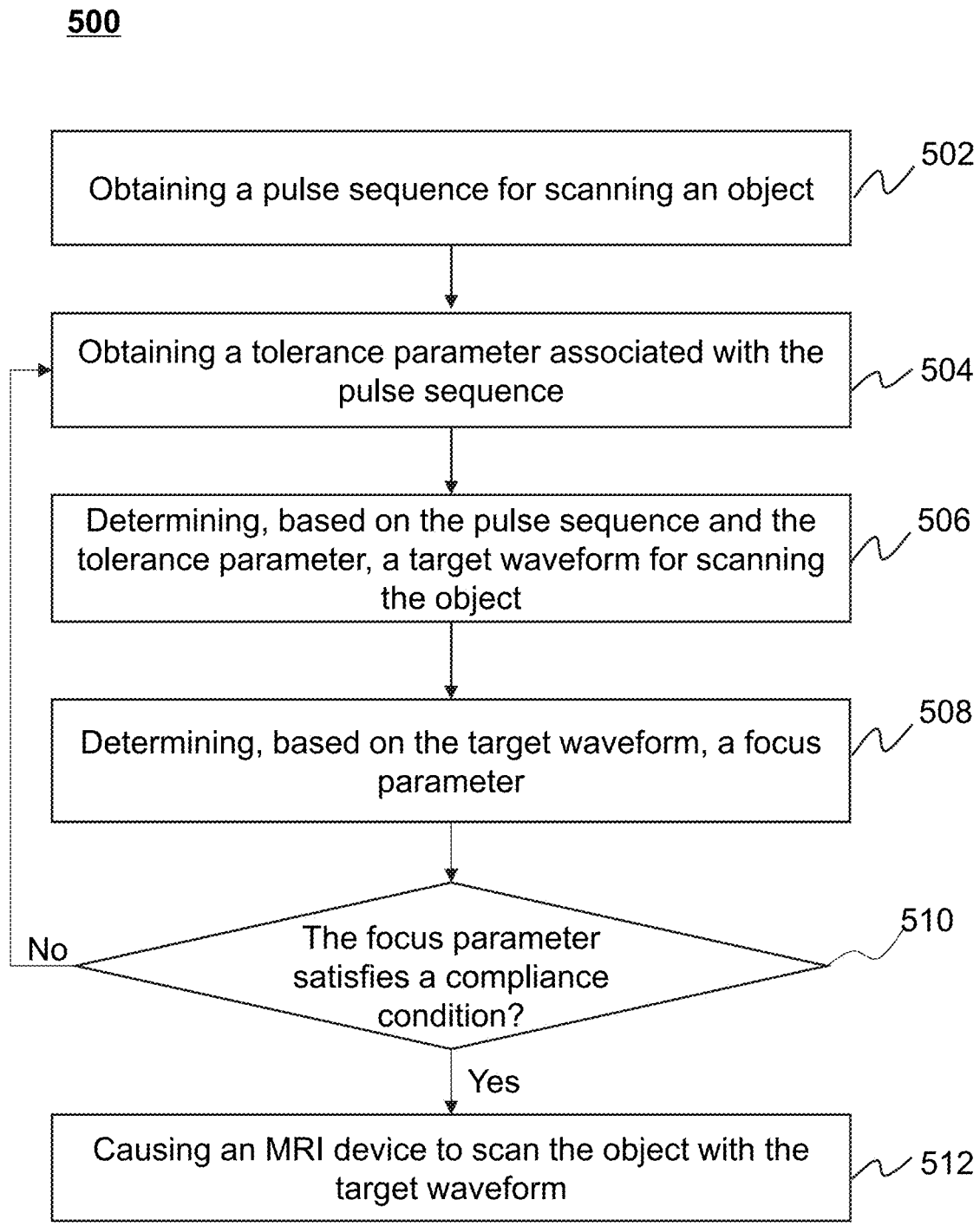
FIG. 5 is a flowchart illustrating an exemplary process for causing an MRI device to scan an object based on a target waveform according to some embodiments of the present disclosure.

FIG. 5 is a flowchart illustrating an exemplary process for causing an MRI device to scan an object based on a target waveform according to some embodiments of the present disclosure. In some embodiments, the process 500 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 502, the processing device 120 (e.g., the obtaining module 410) may obtain a pulse sequence for scanning an object. The object may be biological or non-biological. For example, the object may include a patient, a man-made object, etc., as described elsewhere in the present disclosure (e.g., FIG. 1A and the descriptions thereof).

As used herein, the pulse sequence refers to a set of pulses repeatedly applied by an MRI device during an MRI scan. Factors including, e.g., time intervals between the pulses, the amplitudes, and the shapes of waveforms corresponding to the pulses may affect the generation/reception of MR signals and thus affect the characteristics (e.g., resolution, contrast, etc.) of MR images. In some embodiments, the waveforms corresponding to the pulses of the pulse sequence may refer to an initial waveform of the pulse sequence.

In some embodiments, the pulse sequence may include a radio frequency (RF) pulse sequence, a gradient pulse sequence, or the like, or any combination thereof. The RF pulse sequence may be used to perform an RF excitation on a scanning region of the object (e.g., the patient) to generate corresponding MR signals. The gradient pulse sequence may include an X-gradient pulse signal (e.g., a gradient pulse signal on the gradient axis of the readout direction), a Y-gradient pulse signal (e.g., a gradient pulse signal on the gradient axis of the phase encoding direction), a Z-gradient pulse signal (e.g., a gradient pulse signal on the gradient axis of the slice selection direction), or the like, or any combination thereof. The gradient pulse sequence may be used to add the spatial localization code of the scanning region of the object to the acquired MRI signals. In some embodiments, the pulse sequence may be of different types. For example, the pulse sequence may include a free induction decay (FID) sequence, a spin-echo (SE) sequence, a gradient-echo (GE) sequence, a diffusion sequence, an inversion recovery (IR) sequence, a hybrid sequence, or the like, or any combination thereof.

In some embodiments, the pulse sequence may include one or more first features each of which may affect the generation/reception of the MR signals. Different pulse sequences may include different features. For example, in the case that the pulse sequence is an RF pulse sequence, the one or more first features may include a first frequency range (or bandwidth), a first RF amplitude of each RF pulse, a first time point at which each RF pulse is applied to the object, a first duration period of each RF pulse, or the like, or any combination thereof. As another example, in the case that the pulse sequence is a gradient pulse sequence, the one or more first features may include a first gradient field amplitude (i.e., a maximum value of the gradient field), a first time point at which each gradient pulse is applied to the object, a first duration period of each gradient pulse, a first axis to apply each gradient pulse (also referred to a direction of each gradient pulse), a first rising slope from a minimum value to the maximum value of the gradient field, a first falling slope from the maximum value to the minimum value of the gradient field, or the like, or any combination thereof. In some embodiments, the pulse sequence may further include object information. The object information may include information associated with the object, such as the scanning region, the name, age, gender, medical history, physical examination result, etc. of the object.

In some embodiments, the initial waveform corresponding to the pulse sequence may be defined by the one or more first features. In some embodiments, the first features of the pulse sequence may also be regarded as features (or initial features) of the initial waveform. The type of the initial waveform may correspond to the type of the pulse sequence. For example, an RF pulse sequence may correspond to an RF pulse waveform. As another example, a gradient pulse sequence may correspond to a gradient waveform.

In some embodiments, the pulse sequence may vary according to the scanning region of the object. For example, for the scanning region of the object including the heart of the object, the pulse sequence may be a gradient-echo cine MRI sequence, a gradient echo cardiograph-labeled cine MRI sequence, or a fast imaging with steady-state precession sequence, etc. As another example, for the scanning region of the object including the brain of the object, the pulse sequence may be a 2D SE T1-weighted imaging (T1WI) sequence, a 2D fast spin-echo (FSE) T2-weighted imaging (T2WI) sequence, a diffusion-weighted imaging (DWI) sequence, a susceptibility weighted imaging (SWI) sequence, etc. The processing device 120 may obtain the pulse sequence based on the scanning region of the object. For example, the processing device 120 may obtain a scanning protocol associated with the scanning region of the object from the storage device 130 or an external data source. The processing device 120 may designate a sequence corresponding to the scanning protocol as the pulse sequence. In some embodiments, the pulse sequence may be provided to the processing device 120 by a user (e.g., a doctor) so that the obtaining module 410 may receive the pulse sequence and transfer the pulse sequence to the other components of the processing device 120 for subsequent operations.

In 504, the processing device 120 (e.g., the obtaining module 410) may obtain a tolerance parameter associated with the pulse sequence. As used herein, a tolerance parameter may be any parameter (and/or a value of such a parameter) that may affect the execution of a scan using an MRI device. For example, the tolerance parameter may be a scanning time, an acoustic noise expectation (e.g., expressed in decibel (dB)), a specific absorption rate (SAR, expressed in watts/Kg) or its distribution in the object, or the like. Specifically, the tolerance parameter may be set or adjusted according to practical needs. For example, for a patient with an implant in the body, the SAR in a scanning region, or a portion thereof, or in a vicinity thereof, during the MRI scan may need to conform to standards or regulations since electromagnetic energies absorbed by the patient may have adverse effects on the patient. In this regard, the tolerance parameter may be the SAR. As another example, for a child who cannot tolerate strong noises (i.e., acoustic noises), the tolerance parameter may be the acoustic noise expectation. As a result, noises caused by the MRI device may be controlled under an acoustic noise threshold (also referred to as a compliance condition, i.e., the value of the tolerance parameter). As a further example, for an adult who wants to be scanned quickly, the tolerance parameter may be the scanning time.

In some embodiments, different tolerance parameters may be set with respect to different pulse sequences. For example, the acoustic noise expectation may be designated as the tolerance parameter with respect to a gradient pulse sequence since noises caused by the MRI device are mainly related to gradient coils of the MRI device. As another example, the SAR may be designated as the tolerance parameter with respect to an RF pulse sequence since the absorption of electromagnetic energies by the object is mainly related to RF signals emitted by RF emitting coils of the MRI device.

Figure 8:
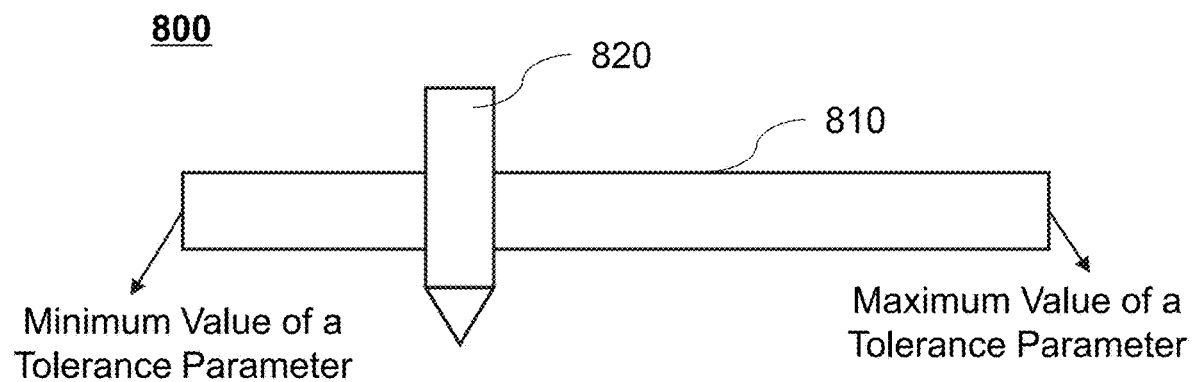
FIG. 8 is a diagram illustrating an exemplary user interface associated with a tolerance parameter and/or a focus parameter according to some embodiments of the present disclosure.

In some embodiments, the tolerance parameter may be set according to a default setting of the MRI system 100 or set by a user or operator via the terminal device 140. For example, after a desired pulse sequence becomes available, the terminal device 140 may subsequently display a user interface configured to allow user interaction. The user may input the tolerance parameter via the user interface. As another example, the user interface may include a scale bar as illustrated in FIG. 8. The user may drag the scale bar to specify the value of the tolerance parameter.

In 506, the processing device 120 (e.g., the waveform determination module 420) may determine a target waveform for scanning the object based on the pulse sequence and the tolerance parameter. The target waveform may be configured to enable the corresponding coils to produce corresponding pulse signals. For example, if the target waveform is an RF pulse waveform, the processing device 120 may cause RF coils to emit RF pulse signals corresponding to the target waveform. As another example, if the target waveform is a gradient waveform, the processing device 120 may cause gradient coils to produce gradient pulse signals corresponding to the target waveform. In some embodiments, the target waveform may represent a current applied to the gradient coils or RF coils of the MRI device with respect to the time.

The target waveform may include one or more target features similar to the initial features of the initial waveform (or the pulse sequence). For example, in the case that the pulse sequence is a gradient pulse sequence, the one or more target features of the target waveform may include a target gradient field amplitude, a target time point at which each gradient pulse is applied to the object, a target duration period of each gradient pulse, a target axis to apply each gradient pulse (also referred to a direction of each gradient pulse), a target rising slope, a target falling slope, or the like, or any combination thereof.

In some embodiments, the processing device 120 may query a waveform database based on the pulse sequence and the tolerance parameter to obtain the target waveform. For example, the waveform database may include a corresponding relationship among the pulse sequence, the tolerance parameter, and the target waveform. The processing device 120 may determine the target waveform based on the pulse sequence, the tolerance parameter, and the corresponding relationship. In some embodiments, the first features of the pulse sequence, and the tolerance parameter may be served as index values to query the waveform database to obtain the target waveform. Specifically, the retrieval of the target waveform from the waveform database including multiple candidate reference target sequences may be the same as or similar to the determination of the initial waveform from a waveform library as described in FIG. 6. The tolerance parameter may be regarded as a particular feature of the pulse sequence. Then the pulse sequence and the tolerance parameter may be regarded as a target sequence possessing the first features and the particular feature (the tolerance parameter). The processing device 120 may determine a target matching degree between the target sequence and each of at least some of the multiple candidate reference target sequences stored in the waveform database. The processing device 120 may determine the target waveform based on a highest target matching degree among the determined target matching degrees between the target sequence and the at least some of the multiple candidate reference target sequences.

As used herein, the waveform database may be predetermined based on a plurality of candidate pulse sequences, and a plurality of candidate tolerance parameters. For example, the processing device 120 (or another processing device external to the MRI system 100) may determine a specific relationship among a candidate pulse sequence, a candidate tolerance parameter, and a corresponding waveform by performing a simulation operation. The specific relationship may be stored in the waveform database.

As another example, if a candidate pulse sequence includes gradient pulse sequences on the X-axis, the Y-axis, and the Z-axis, respectively, and a candidate tolerance parameter is the acoustic noise expectation, the noises caused by the MRI device may be modeled as a linear time-invariant system. Therefore, a relationship between gradient waveforms (also referred to as a candidate target waveform) corresponding to the gradient pulse sequences and a value of the acoustic noise expectation may be denoted as Equation (1) as follows:

$$P = H(x)*G(x) + H(y)*G(y) + H(z)*G(z), \tag{1}$$

where P denotes the acoustic noise expectation, $H(x)$ denotes an acoustic transfer function of X-gradient coils, $H(y)$ denotes an acoustic transfer function of Y-gradient coils, $H(z)$ denotes an acoustic transfer function of Z-gradient coils, $G(x)$ denotes a gradient waveform applied on the X-gradient coils, $G(y)$ denotes a gradient waveform applied on the Y-gradient coils, $G(z)$ denotes a gradient waveform applied on the Z-gradient coils, and * denotes a convolution operation. As used herein, the acoustic transfer functions $H(x)$, $H(y)$, and $H(z)$ may be predetermined by measuring the frequency response functions of the X-gradient coils, the Y-gradient coils, and the Z-gradient coils, respectively. A plurality of candidate target waveforms may be determined according to Equation (1) based on the plurality of candidate pulse sequences and the plurality of candidate tolerance parameters. Each candidate target waveform may correspond to a candidate acoustic noise expectation and a candidate pulse sequence. In some embodiments, when the pulse sequence is a gradient pulse sequence, the processing device 120 may determine the target waveform according to Equation (1) based on the gradient pulse sequence and the acoustic noise expectation directly.

In some embodiments, the processing device 120 may determine the initial waveform based on a relationship between a specific pulse sequence and a specific initial waveform. Each specific pulse sequence may correspond to a specific initial waveform. In some embodiments, the relationship between the specific pulse sequence and the specific initial waveform may be presented by an equation, such as Equation (1). In some embodiments, the processing device 120 may query a waveform library based on the pulse sequence to obtain a query result. The processing device 120 may determine the initial waveform based on the query result. More descriptions regarding the determining of the initial waveform from the waveform library may be found elsewhere in the present disclosure (e.g., FIG. 6 and the descriptions thereof).

Figure 9A:
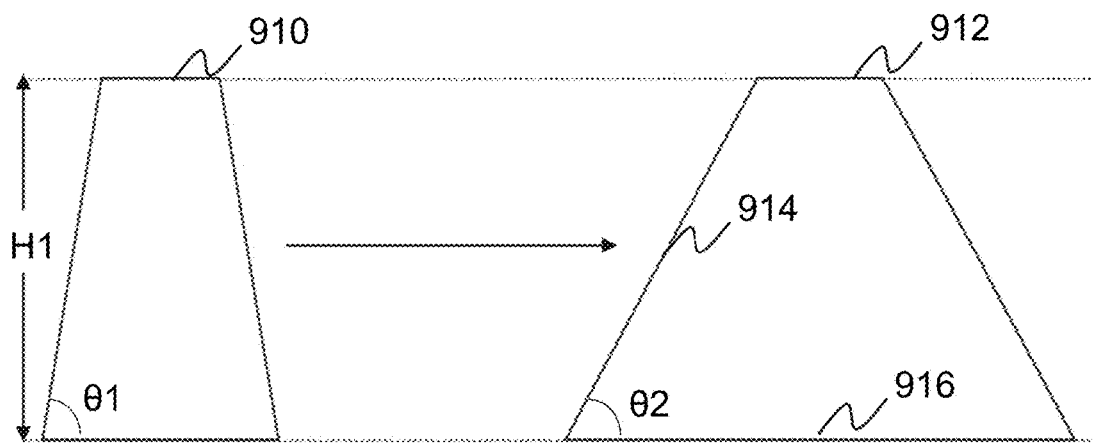
FIG. 9A is a schematic diagram illustrating an exemplary process for adjusting a gradient waveform for reducing a noise caused by gradient coils of an MRI device according to some embodiments of the present disclosure.
Figure 9B:
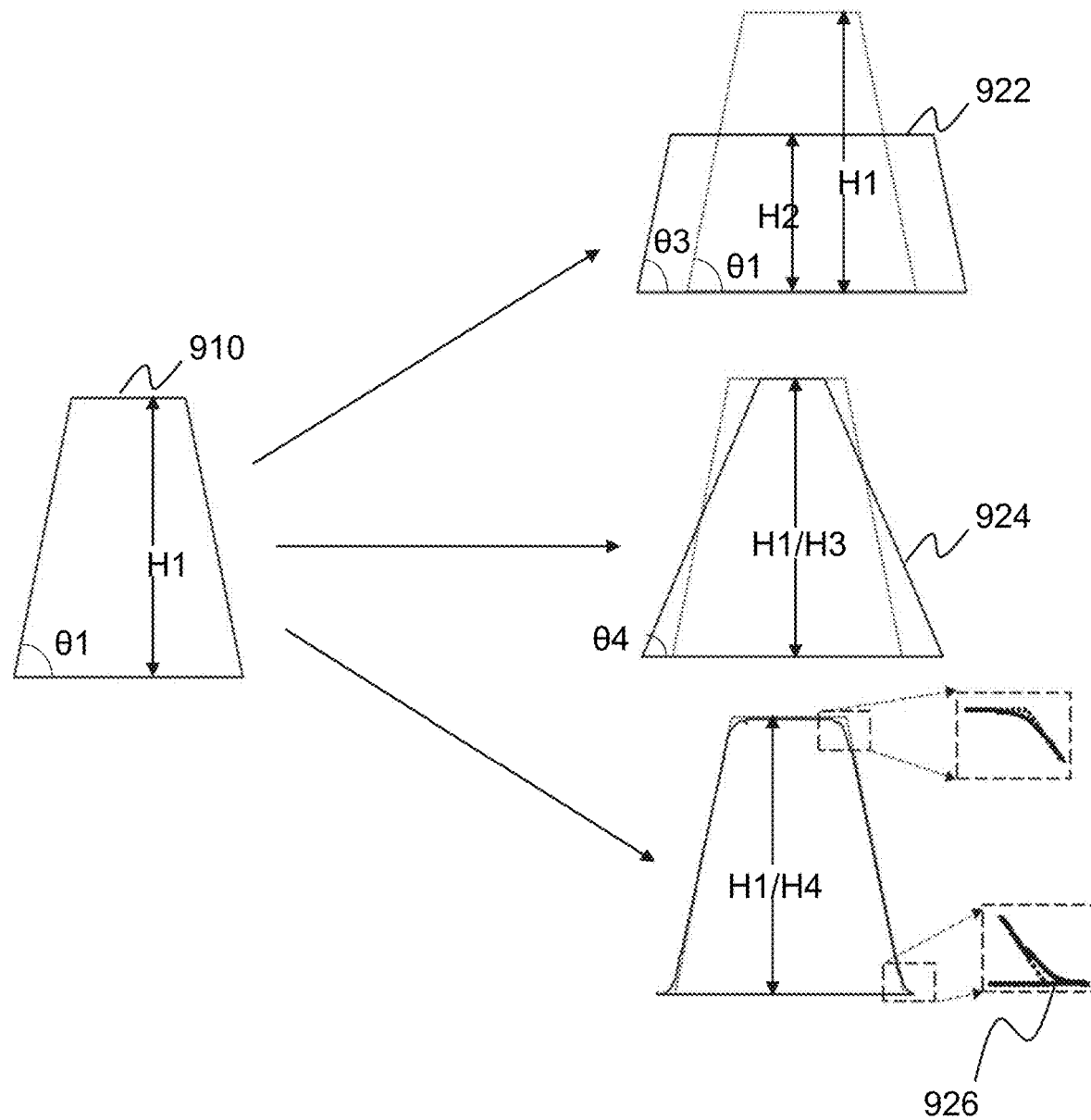
FIG. 9B is a schematic diagram illustrating an exemplary process for adjusting a gradient waveform for reducing a noise caused by gradient coils of an MRI device according to some embodiments of the present disclosure.

The processing device 120 may determine the target waveform by adjusting the initial waveform based on the tolerance parameter. For example, the processing device 120 may adjust one or more waveform parameters of the initial waveform based on the tolerance parameter. The one or more waveform parameters of the initial waveform may include a pulse amplitude, a pulse phase, a slope, or a profile, or the like, or any combination thereof. In some embodiments, the one or more waveform parameters may be expressed as features of the target waveform. For example, the profile of the initial waveform may include the rising/falling slope of the initial waveform. As another example, the pulse amplitude of the initial waveform may be set as the RF amplitude with respect to the RF pulse sequence or the gradient field amplitude with respect to the gradient pulse sequence. Specifically, if the tolerance parameter includes the acoustic noise expectation corresponding to a gradient pulse sequence, the acoustic noises of the MRI device may be reduced by adjusting the gradient waveform of the corresponding gradient pulse sequence. For example, as shown in FIG. 9A, the acoustic noises may be reduced by maintaining the gradient field amplitude of the gradient waveform and reducing the rising/falling slope of the gradient waveform. As another example, as shown in FIG. 9B, the acoustic noises may be reduced by maintaining a gradient area of the gradient waveform and reducing the gradient field amplitude (illustrated as waveform 922) and/or the rising/falling slope (illustrated as waveform 924) of the gradient waveform. In some embodiments, when the tolerance parameter includes the SAR corresponding to an RF pulse sequence, the SAR or its distribution in the object may be adjusted by adjusting, for example, the pulse phase, of the corresponding RF pulse waveform.

In some embodiments, the processing device 120 may store the pulse sequence, the tolerance parameter, the corresponding target waveform, and/or the object information into a storage device (e.g., the storage device 130) for subsequent operations. In some embodiments, when storing the obtained target waveform into the storage device, in order to avoid that the storage device stores the same target waveforms for multiple times, the processing device 120 may further determine whether the target waveform already exists, thereby saving storage resources of the storage device.

In 508, the processing device 120 (e.g., the verification module 430) may determine a focus parameter based on the target waveform.

The focus parameter may be a parameter correlating with the tolerance parameter. For example, the focus parameter may include a scanning time, an acoustic noise expectation (e.g., expressed in decibel (dB)), a specific absorption rate (SAR, expressed in watts/Kg), or the like.

In some embodiments, the values of a tolerance parameter and a corresponding focus parameter may be negatively correlated. The lower (the value of) the tolerance parameter is, the greater (the value of) the focus parameter may be. For example, for a gradient pulse sequence, if the tolerance parameter is the acoustic noise expectation corresponding to the gradient pulse sequence, the focus parameter may be the scanning time. The weaker the noises of the MRI device is, the longer the scanning time may be. As another example, if the tolerance parameter is the SAR corresponding to an RF pulse sequence, the focus parameter may be the scanning time. The smaller the SAR is, the longer the scanning time may be. As a further example, if the tolerance parameter is the scanning time corresponding to a gradient pulse sequence and/or an RF pulse sequence, the tolerance parameter may be the acoustic noise expectation and/or the SAR. The greater the acoustic noise expectation and/or the SAR is, the longer the scanning time may be.

In 510, the processing device 120 (e.g., the verification module 430) may determine whether the focus parameter satisfies a compliance condition. In response to determining that the focus parameter fails to satisfy the compliance condition, the processing device 120 may proceed to perform operation 504. In response to determining that the focus parameter satisfies the compliance condition, the processing device 120 may proceed to perform operation 512.

In some embodiments, the compliance condition may be a threshold corresponding to the focus parameter. For example, if the tolerance parameter is the acoustic noise expectation, the focus parameter may be the scanning time. The compliance condition may be a scanning time threshold, for example, 3 minutes, 4 minutes, 5 minutes, 6 minutes, etc. In response to determining that the scanning time (i.e., the focus parameter) is greater than the scanning time threshold, the processing device 120 may determine that the focus parameter fails to satisfy the compliance condition. In response to determining that the scanning time is less than (or equal to) the scanning time threshold, the processing device 120 may determine that the focus parameter satisfies the compliance condition. In some embodiments, when the scanning time (i.e., the focus parameter) is greater than the scanning time threshold, the processing device 120 may feedback the scanning time to the user, for example, displaying the value of the scanning time on the terminal device 140. The user may adjust (e.g., increase/decrease) the acoustic noise expectation (i.e., the tolerance parameter) to reduce the scanning time. The processing device 120 may determine an updated target waveform based on the pulse sequence and the adjusted acoustic noise expectation.

In some embodiments, if the user accepts the focus parameter, for example, the user clicks a button indicating that the tolerance parameter is accepted, the processing device 120 may determine that the focus parameter satisfies the compliance condition. If the user does not accept the focus parameter, for example, the user clicks a button indicating that the tolerance parameter is not accepted, the processing device 120 may determine that the focus parameter does not satisfy the compliance condition.

Figure 10A:
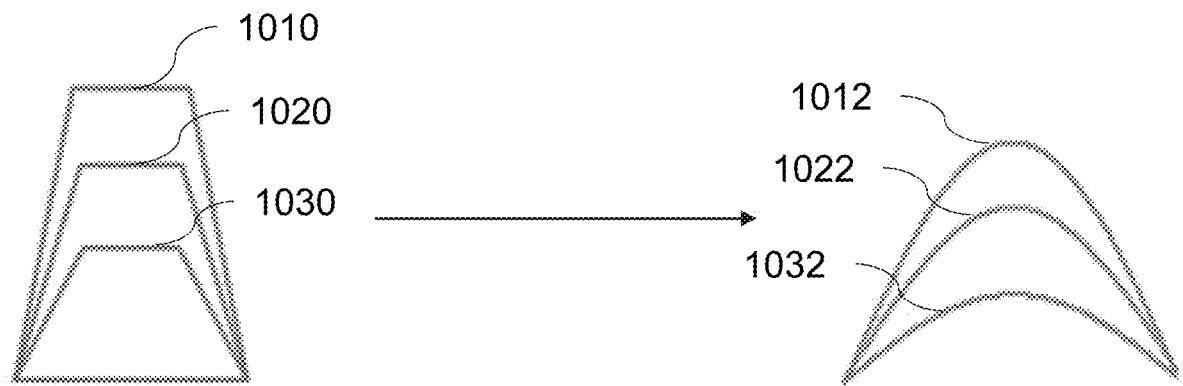
FIG. 10A is a schematic diagram illustrating an exemplary process for adjusting a waveform according to some embodiments of the present disclosure.
Figure 10B:
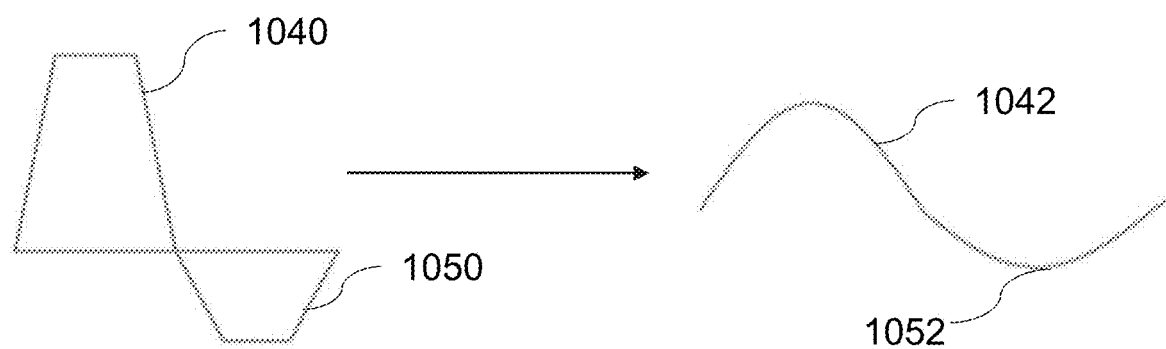
FIG. 10B is a schematic diagram illustrating an exemplary process for adjusting a waveform according to some embodiments of the present disclosure.

In some embodiments, when the focus parameter fails to satisfy the compliance condition, the processing device 120 may also adjust the target features of the target waveform. Different adjustment strategies may be used with respect to different types of the target waveform. For example, if the target waveform is an RF pulse waveform, the adjustment strategy for adjusting the target features of the target waveform may include adjusting an RF amplitude, a bandwidth, etc. If the target waveform is a gradient waveform, the adjustment strategy for adjusting the target features of the target waveform may include adjusting a gradient field amplitude, a rising/falling slope, a profile (e.g., as shown in FIGS. 10A and 10B), etc. In some embodiments, the processing device 120 may adjust the target features of the target waveform according to practical needs. For example, the processing device 120 may obtain a plurality of adjusted target waveforms by adjusting one or more of the target features. The processing device 120 may determine an updated focus parameter corresponding to each adjusted target waveform. The processing device 120 may cause the MRI device to scan the object based on an adjusted target waveform corresponding to an updated focus parameter with the smallest value.

In 512, the processing device 120 (e.g., the control module 440) may cause the MRI device to scan the object based on the target waveform. It should be noted that, once the MRI device starts to scan the object, the target waveform cannot be adjusted until the scan terminates upon completion or is interrupted (e.g., according to a user instruction). The processing device 120 may transmit the target waveform to a driving unit for executing the target waveform. Exemplary driving units may include a field programmable gate array (FPGA), a digital signal process (DSP) chip, etc.

In some embodiments, the target waveform may include one or more gradient waveforms. The processing device 120 may initiate gradient channels of the MRI device corresponding to the one or more gradient waveforms. The gradient channel(s) may include an X-axis gradient channel (corresponding to the X-axis gradient coils), a Y-axis gradient channel (corresponding to the Y-axis gradient coils), or a Z-axis gradient channel (corresponding to the Z-axis gradient coils), or the like, or any combination thereof. The processing device 120 may cause the corresponding gradient coils to transmit the gradient waveforms using the corresponding gradient channels. In some embodiments, all the gradient channels may simultaneously transmit the corresponding gradient waveforms to perform the first-order shimming, the second-order shimming, the third-order shimming, or the high-order shimming to obtain a uniform gradient field.

In some embodiments, the target waveform may include one or more RF pulse waveforms. The processing device 120 may perform a pulse frequency modulation on at least one of the one or more RF pulse waveforms. As used herein, the pulse frequency modulation refers to adjusting the frequency of an RF pulse to the resonance frequency of the MRI device since the MRI device can excite the corresponding atoms (e.g., protons) and receive the resultant MR signals only when the frequency of the RF pulse is consistent with the resonance frequency of the MRI device. For example, when the main magnetic field of the MRI device is 1.5 tesla (T), the center resonance frequency of the main magnetic field may be about 64 MHz. When the main magnetic field of the MRI device is 3.0 T, the center resonance frequency of the main magnetic field may be about 128 MHz. The processing device 120 may initiate RF transmission channels of the MRI device each of which corresponds to an RF pulse waveform. The processing device 120 may transmit the modulated RF pulse waveforms using the corresponding RF transmission channels simultaneously. The processing device 120 may cause RF coils corresponding to each transmission channel to emit RF signals corresponding to the RF pulse waveform. For example, when the MRI device includes eight sets of RF emitting coils, the processing device 120 may obtain an RF pulse sequence including eight RF sub-sequences each of which corresponds to an RF sub-pulse waveform. Each RF sub-sequence may correspond to an RF transmission channel, i.e., each RF sub-pulse waveform may be emitted through one RF transmission channel. In some embodiments, the count or number of the RF transmission channels may be determined based on the main field of the MRI device. For example, the count or number of the RF transmission channels may be 8, 16, 32, 64, etc.

In some embodiments, the target waveform may include a gradient waveform and an RF pulse waveform. The processing device 120 may initiate the corresponding RF transmission channel and the corresponding gradient channel. The processing device 120 may transmit the corresponding waveform using the corresponding transmission channels.

In some embodiments, the processing device 120 may obtain MR signals of the object based on the target waveform. The processing device 120 may generate an MR image of the object by reconstructing the MR signals. The processing device 120 may determine whether an image quality of the MR image meets a quality threshold. As used herein, the quality threshold may be assessed in terms of a signal-to-noise ratio (SNR), an image resolution, an image contrast, or the like, or a combination thereof. In response to determining that an image quality of the MR image does not meet the quality threshold, the processing device 120 may adjust the waveform parameters and/or the tolerance parameter. One or more parameters may be adjusted. The one or more parameters to be adjusted may be the same as or different from at least one parameter that is adjusted in a prior adjustment when the target waveform is determined according to some embodiments of the present disclosure as described in, e.g., 506 and 510. For example, when an adjustment strategy used in a prior adjustment is to adjust the pulse amplitude, the processing device 120 may adjust the profile of the initial waveform. As another example, when an adjustment strategy used in a prior adjustment is to adjust the slope of the initial waveform, the processing device 120 may adjust the pulse amplitude and/or the profile of the initial waveform. As a further example, after adjusting the waveform parameters multiple times, and the obtained MR image still does not meet the quality threshold, the processing device 120 may adjust the tolerance parameter.

In some embodiments, the processing device 120 may obtain a target MR image of the object by weighting MR images corresponding to different adjustment strategies. For example, the processing device 120 may assign a relatively high weight coefficient to an MR image that is closer to the quality threshold, and assign a relatively low weight coefficient to an MR image that is far from the quality threshold. The processing device 120 may determine the target MR image based on the weight coefficients. As another example, the processing device 120 may determine the target MR image by averaging MR images obtained by different adjustment strategies.

It should be noted that, according to the process 500, by scanning the object based on the target waveform obtained according to the tolerance parameter and the pulse sequence, the tolerance parameter (e.g., the acoustic noise expectation, the SAR, etc.) in the MRI process may be controlled by a user set. In addition, the focus parameter (e.g., the scanning time) and the tolerance parameter (e.g., the acoustic noise expectation, the SAR, etc.) may be balanced by setting different tolerance parameters, thereby improving the user experience.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 508 and operation 510 may be omitted. As another example, the processing device 120 may store the pulse sequence, the tolerance parameter, the corresponding target waveform, the corresponding focus parameter, and/or the object information into the waveform database for subsequent operations. After obtaining the pulse sequence and the tolerance parameter, the processing device 120 may first query the waveform database to determine the corresponding target waveform and/or the corresponding focus parameter. In some embodiments, the waveform database and/or the waveform library may be obtained by another device or system other than the MRI system 100, e.g., a device or system of a vendor of a manufacturer.

Figure 6:
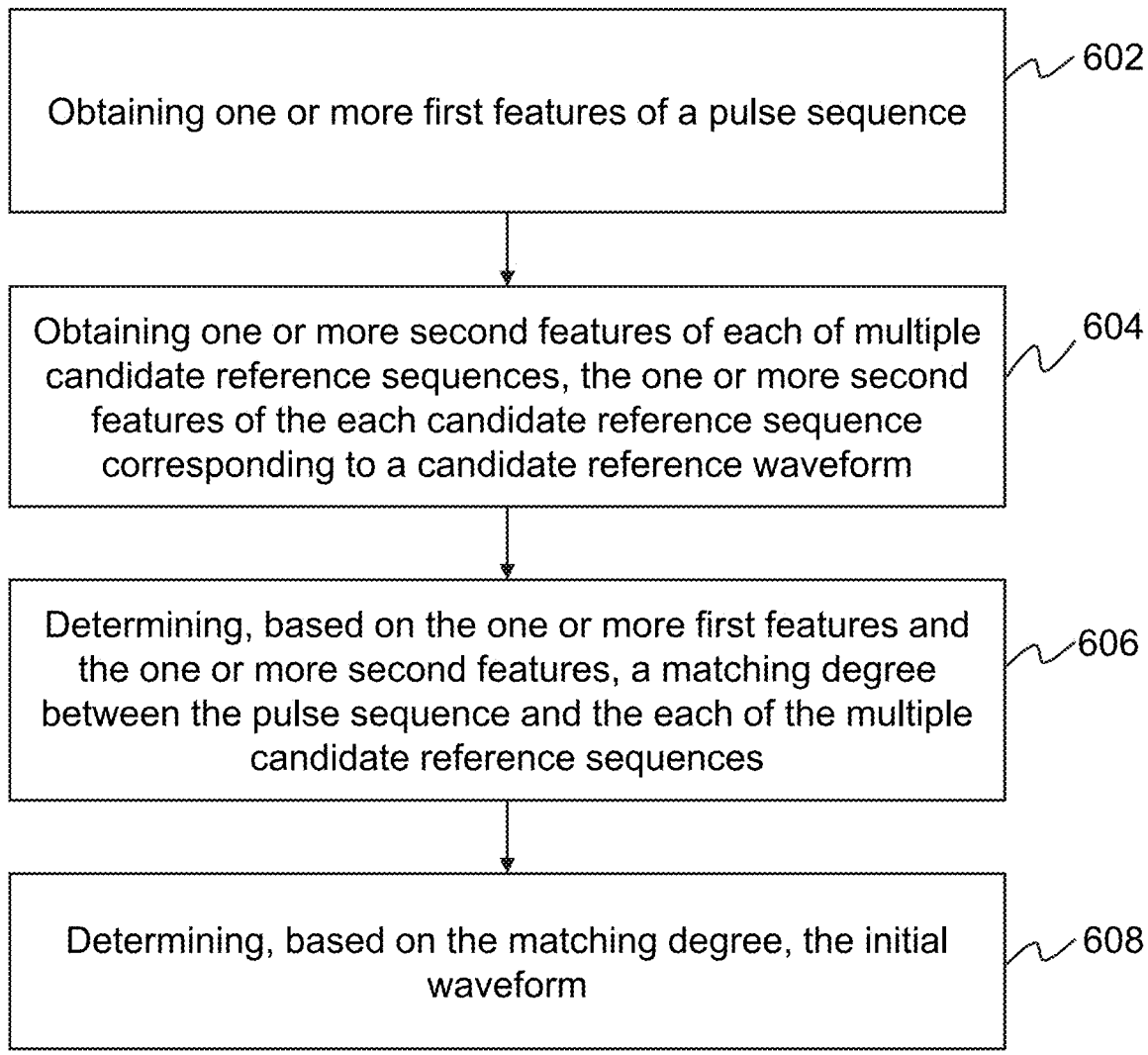
FIG. 6 is a schematic flowchart illustrating an exemplary process for determining a waveform corresponding to a pulse sequence from a waveform library according to some embodiments of the present disclosure.

FIG. 6 is a schematic flowchart illustrating an exemplary process for determining a waveform corresponding to a pulse sequence from a waveform library according to some embodiments of the present disclosure. In some embodiments, the process 600 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting. In some embodiments, the initial waveform and/or the target waveform described elsewhere in the present disclosure (e.g., operation 506 illustrated in FIG. 5) may be obtained according to the process 600.

In 602, the processing device 120 (e.g., the waveform determination module 420) may obtain one or more first features of a pulse sequence. The pulse sequence may include a radio frequency (RF) pulse sequence, a gradient pulse sequence, etc. as described elsewhere in the present disclosure (e.g., FIG. 5 and the descriptions thereof). In some embodiments, a user may specify the one or more first features via, e.g., the terminal device 140. In some embodiments, the one or more first features may be retrieved from the storage device 130, or any other storage device. For example, a user may store the pulse sequence and the corresponding first features in the storage device 130, or any other storage device. The processing device 120 may obtain the first features corresponding to the pulse sequence from the storage device 130, or any other storage device. As another example, the one or more first features may be inputted by a user (e.g., a doctor) via the terminal device 140 directly.

As used herein, the pulse sequence for scanning an object may correspond to an initial waveform. The pulse sequence may include one or more first features that may define the initial waveform corresponding to the pulse sequence. The one or more first features of the pulse sequence may also be regarded as features of the initial waveform. In some embodiments, if the pulse sequence is an RF pulse sequence, the one or more first features may include a first frequency range (or bandwidth), a first RF amplitude of each RF pulse, a first time point at which each RF pulse is applied to the object, a first duration period of each RF pulse, or the like, or any combination thereof. In some embodiments, if the pulse sequence is a gradient pulse sequence, the one or more first features may include a first gradient field amplitude, a first time point at which each gradient pulse is applied to the object, a first duration period of each gradient pulse, a first direction of each gradient pulse, a first rising slope, a first falling slope, or any combination thereof.

In some embodiments, the one or more first features may further include the type of the pulse sequence (also referred to as a first type) and/or information of the object (also referred to as object information, e.g., scanning region, the name, age, gender, medical history, physical examination result, etc. of the object).

In 604, the processing device 120 (e.g., the waveform determination module 420) may obtain one or more second features of each of multiple candidate reference sequences. A candidate reference sequence may include a second type and/or load information (i.e., information of a subject being scanned by an MRI device based on the candidate reference sequence). A set of second features of the each candidate reference sequence may correspond to a candidate reference waveform. The multiple candidate reference sequences (and optionally additional candidate reference sequences) may be stored in a waveform library. The candidate reference sequences to be analyzed in 604 and/or beyond in one or more subsequent operations of FIG. 6 may be all or a portion of the candidate reference sequences in the waveform library. For instance, a portion of the candidate reference sequences in the waveform library may be selected, based on a selection rule, to be analyzed in 604 and/or beyond. The selection rule may relate to a first feature of the pulse sequence and a corresponding second feature of a candidate reference sequence of the waveform library. An exemplary selection rule is that a candidate reference sequence of the waveform library whose one or more second features be the same as or close to (e.g., the deviation being below 50%, 40%, 30%, 20%, etc.) the corresponding first feature(s) of the pulse sequence is selected as a candidate reference sequence for further analysis according to 604 and/or beyond. Another exemplary selection rule is that the type of a candidate reference sequence (e.g., a gradient pulse, an RF pulse) is the same as the type of the pulse sequence.

The waveform library may be determined in the same or similar way as the waveform database as described in operation 506 in FIG. 5. In some embodiments, the waveform library and the waveform database may be a same database. In some embodiments, when the first type of pulse sequence and the second type of candidate reference sequence are the same (e.g., both being a gradient pulse sequence or an RF pulse sequence), each first feature may correspond to one second feature of the set of the second features.

As used herein, a candidate reference sequence may refer to a known pulse sequence. That is, the second features and a candidate reference waveform of the candidate reference sequence may be known. For example, the candidate reference sequence may be a pulse sequence that has been used to scan a subject (e.g., a same patient, or a different patient)

and then stored in the waveform library. As another example, the candidate reference sequence may be a pulse sequence obtained by performing a simulation operation.

In 606, the processing device 120 (e.g., the waveform determination module 420) may determine, based on the one or more first features and the one or more second features, a matching degree between the pulse sequence and each of the multiple candidate reference sequences.

The processing device 120 may determine multiple matching degrees between the pulse sequence and the multiple candidate reference sequences. For example, the waveform library may include three candidate reference sequences to be analyzed further, e.g., a first candidate reference sequence, a second candidate reference sequence, and a third candidate reference sequence. The corresponding second features of the three candidate reference sequence may be a first set of second features, a second set of second features, and a third set of second features. The processing device 120 may match the first features with the first set of second features, the second set of second features, and the third set of second features, respectively, to obtain three matching degrees, i.e., a first matching degree, a second matching degree, and a third matching degree.

For a specific candidate reference sequence, the processing device 120 may match the first features of the pulse sequence and the specific second features of the specific candidate reference sequence to obtain a specific matching degree. As used herein, the matching the first features with the specific second features may refer to comparing each first feature and the corresponding specific second feature. For example, when both the pulse sequence and the specific candidate reference sequence are of the same type (e.g., both being an RF pulse sequence), and the first features of the pulse sequence may include a first bandwidth, a first RF amplitude, a first duration period, and the specific features of the specific candidate reference sequence may include a second bandwidth, a second RF amplitude, and a second duration period. The processing device 120 may compare the first bandwidth with the second bandwidth, the first RF amplitude with the second RF amplitude, and the first duration period with the second duration period, respectively. The processing device 120 may determine similarity degrees between the first features and the specific second features based on the comparison results. As used herein, the similarity degree may indicate how close the first feature is to the corresponding specific second feature. The processing device 120 may determine the specific matching degree between the pulse sequence and the specific candidate reference sequence based on the similarity degrees. For example, the processing device 120 may determine an average value of the similarity degrees as the specific matching degree. As another example, the processing device 120 may assign a weight to each similarity degree. The processing device 120 may determine the specific matching degree based on the similarity degrees and their respective weights.

In some embodiments, the processing device 120 may match the first features of the pulse sequence and the second features of each candidate reference sequence based on a matching rule. As used herein, the matching rule refers to a file or list specifying one or more features needed to be matched (also referred to as matching features). Specifically, the processing device 120 may obtain the corresponding matching features from the first features of the pulse sequence and the second features of each candidate reference sequence. The processing device 120 may determine the matching degree based on the matching features. For example, if the matching features include the amplitude and the duration of pulse, the processing device 120 may obtain a first amplitude and a first duration from the first features. The processing device 120 may obtain a second amplitude and a second duration from the second features. The processing device 120 may match the first amplitude with the second amplitude, and the first duration with the second duration, respectively, to obtain the matching degree. Therefore, when the matching degree is obtained based on the matching rule, the processing device 120 does not need to match each first feature with the corresponding second feature, thereby saving the processing time and improving efficiency.

In some embodiments, before matching the first features and the specific second features, the processing device 120 may determine whether the first type and the second type are the same, and/or the processing device 120 may match the object information with the load information of the specific candidate reference sequence. In response to determining that the type of the pulse sequence is different from the type of the specific candidate reference sequence, and/or the object information is different from the load information of the specific candidate reference sequence, the processing device 120 may determine that the specific matching degree has the minimum value. In other words, the specific candidate reference sequence may be removed from the matching analysis. In response to determining that the type of the pulse sequence is the same as the type of the specific candidate reference sequence, and/or the object information is the same as the load information of the specific candidate reference sequence, the processing device 120 may further match the first features of the pulse sequence and the specific second features of the specific candidate reference sequence.

In some embodiments, the pulse sequence may include one or more sub-sequences. Each sub-sequence may correspond to a transmission channel. For example, for an MRI device that uses multiple RF transmission channels for parallel transmission, each RF transmission channel may correspond to an RF pulse sub-sequence. The processing device 120 may match each of the one or more sub-sequences with a candidate reference sequence. In some embodiments, most features of the one or more sub-sequences corresponding to different transmission channels may be the same, while only a few features of the transmission channels may be different. Therefore, the first features of the pulse sequence may be divided into a common feature and a channel-specific feature. As used herein, a common feature refers to a feature that each sub-sequence has the same value. As used herein, a channel-specific feature refers to a feature regarding which at least some of the one or more sub-sequences have different values. For example, if the different feature between RF pulse sub-sequences of an RF pulse sequence is the phase, and the same feature between the RF sub-sequences is the RF amplitude, the processing device 120 may designate the RF amplitude as the common feature, and designate the phase as the channel-specific feature. The processing device 120 may match the common feature of any one of a sub-sequence with the corresponding second feature of each candidate reference sequence (or each candidate reference waveform). The processing device 120 may match the channel-specific feature of each sub-sequence with the corresponding second feature of each candidate reference sequence (or each candidate reference waveform), respectively. For example, for an RF pulse sequence, if the common feature of RF pulse sub-sequences corresponding to RF transmission channels is the phase, and the channel-specific feature of the RF pulse sub-sequences corresponding to the RF transmission channels is the RF amplitude, the processing device 120 may match the phase of any one of the RF pulse sub-sequences with the phase of each of candidate reference RF pulse sub-sequences of a candidate reference RF pulse sequence. The processing device 120 may match the RF amplitude of each of the RF pulse sub-sequences with the RF amplitude of each of the candidate reference RF pulse sub-sequences, respectively. In some embodiments, the candidate reference sequence may include one or more candidate reference sub-sequences. The number or count of the candidate reference sub-sequences of the candidate reference sequence may be the same as the number or count of the sub-sequences of the pulse sequence. The processing device 120 may match each sub-sequence with each candidate reference sub-sequence. In some embodiments, a second common feature of the one or more candidate reference sub-sequences may be the same as a first common feature of the one or more sub-sequences of the pulse sequence. The processing device 120 may match the first common feature and the second common feature only once. For example, if the common feature of both the sub-sequences and the candidate reference sub-sequences is the phase, the processing device 120 may match the phase of any one of the sub-sequences with the phase of any one of the candidate reference sub-sequences. The processing device 120 may fuse matching results to obtain the matching degree based on matching results of sub-sequences with candidate reference sequences (or candidate reference sub-sequences). For example, the processing device 120 may average the matching results of the phase and/or the RF amplitude. In such a case, the amount of calculation that the processing device 120 needs to perform may be reduced, which may achieve a real-time execution.

In 608, the processing device 120 (e.g., the waveform determination module 420) may determine, based on the matching degree, the initial waveform.

In some embodiments, the processing device 120 may identify a highest matching degree among the matching degrees between the pulse sequence and the multiple candidate reference sequences that are analyzed. The processing device 120 may determine, based on a reference waveform corresponding to the reference sequence of the highest matching degree, the initial waveform. For example, the processing device 120 may compare the pulse sequence and a reference sequence of the highest matching degree. The processing device 120 may determine, based on a reference waveform corresponding to the reference sequence and a comparison result, the initial waveform. More descriptions about the determination of the initial waveform may be found elsewhere in the present disclosure (e.g., FIG. 7 and the descriptions thereof).

In some embodiments, the processing device 120 may store the pulse sequence, and the corresponding initial waveform in a storage device (e.g., the storage device 130) for subsequent operations. In some embodiments, when storing the obtained initial waveform into the storage device, in order to avoid that the storage device stores the same initial waveforms for multiple times, the processing device 120 may further determine whether the initial waveform already exists, thereby saving storage resources of the storage device. Specifically, the processing device 120 may determine whether the initial waveform is obtained by adjusting a reference waveform of a highest matching degree. In response to determining that the initial waveform is obtained by adjusting the reference waveform of the highest matching degree, the processing device 120 may store the initial waveform and the corresponding pulse sequence into the storage device. In response to determining that the initial waveform is obtained without adjusting the reference waveform with respect to its original form as retrieved from the waveform library, the processing device 120 may omit storing the initial waveform and the corresponding pulse sequence in the storage device. In some embodiments, the processing device 120 may store the initial waveform that is obtained by directly performing a calculation based on the pulse sequence.

According to the process 600, the initial waveform corresponding to the pulse sequence may be determined by querying the waveform library based on the first features of the pulse sequence (or the initial waveform), thereby improving the scanning efficiency of the MRI device. It is because the waveform content of the initial waveform has a large amount of data, so if the initial waveform is directly calculated based on the pulse sequence, a lot of resources and time may be consumed. However, by determining the initial waveform by matching the pulse sequence with the multiple candidate reference sequences from the waveform library, the resource and time consumption may be reduced and the efficiency for determining the initial waveform may be improved.

It should be noted that the above descriptions are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 602 and operation 604 may be combined into a single operation. As another example, one or more other optional operations (e.g., a storing operation) may be added elsewhere in the process 600. As a further example, the processing device 120 may store information and/or data (e.g., the pulse sequence, the one or more first features, the multiple candidate reference sequences, the one or more second features, the multiple candidate reference waveforms, etc.) associated with the MRI system 100 in a storage device (e.g., the storage device 130) disclosed elsewhere in the present disclosure.

In some embodiments, during an MRI scan, a waveform of a pulse in the pulse sequence may also be stored in the waveform library after being executed. The processing device 120 may query the waveform library to obtain waveforms corresponding to the pulses to be executed during the MRI scan. For example, during an MRI scan, the pulse sequence includes a pulse 1, a pulse 2, a pulse 3, a pulse 4, . . . , and a pulse N in a time sequence. The processing device 120 may determine a waveform 1 corresponding to the pulse 1 based on a relationship between the pulse 1 and the waveform 1. After being executed, the processing device 120 may store each waveform and the corresponding pulse (including one or more corresponding features) into the waveform library. When a pulse M (M<N) is to be executed, the processing device 120 may first query the waveform library to determine the corresponding waveform M. For example, the waveform M may be determined by revising one or more waveforms retrieved from the waveform library that correspond to pulses similar to the pulse M. If there is no corresponding waveform M, the processing device 120 may determine the waveform M without relying on the waveforms already in the waveform library.

Figure 7:
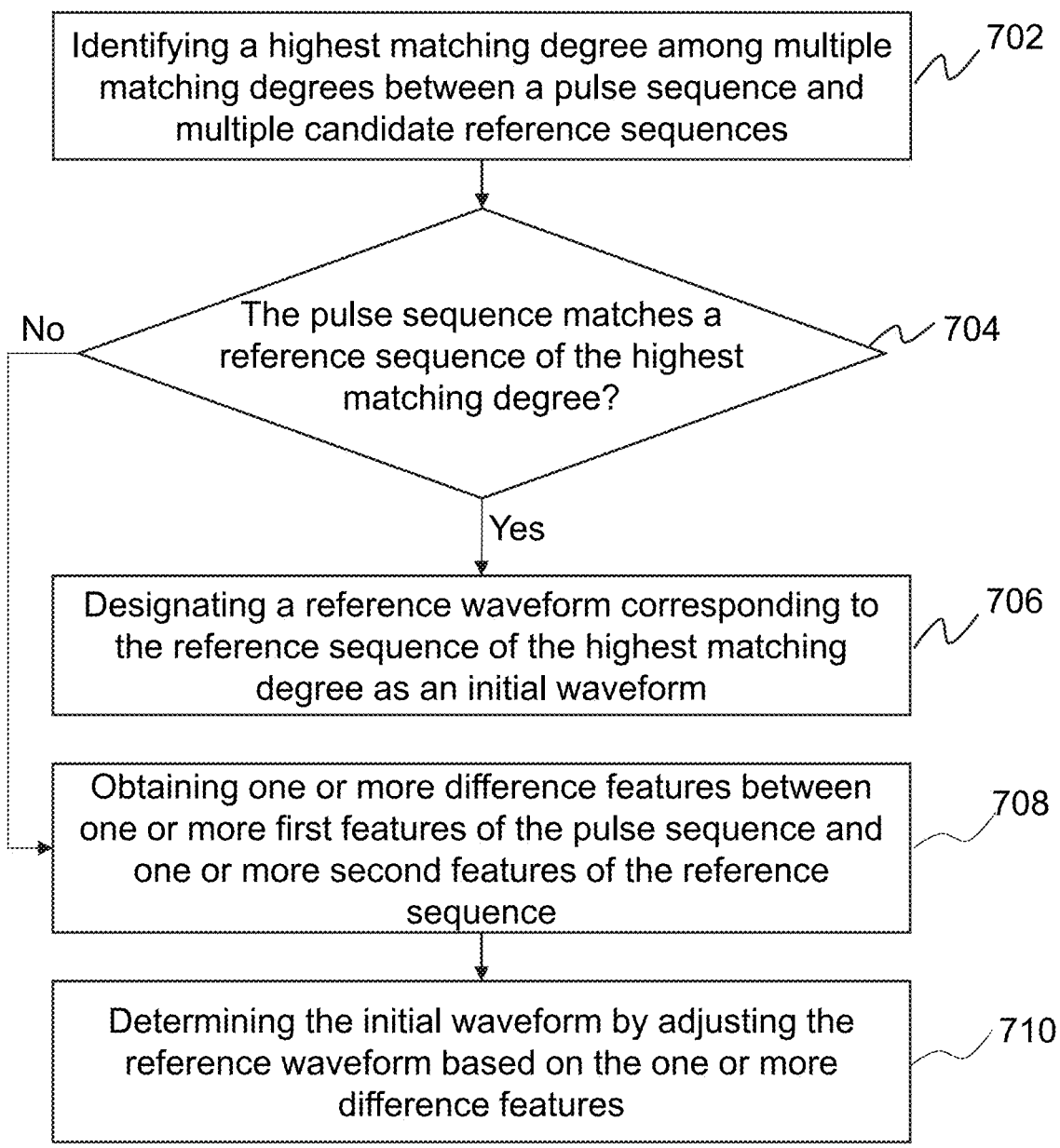
FIG. 7 is a schematic flowchart illustrating an exemplary process for determining an initial waveform corresponding to a pulse sequence from a waveform library according to some embodiments of the present disclosure.

FIG. 7 is a schematic flowchart illustrating an exemplary process for determining an initial waveform corresponding to a pulse sequence from a waveform library according to some embodiments of the present disclosure. In some embodiments, the process 700 may be implemented as a set of instructions (e.g., an application) stored in the storage device 130, storage 220, or storage 390. The processing device 120, the processor 210 and/or the CPU 340 may execute the set of instructions, and when executing the instructions, the processing device 120, the processor 210 and/or the CPU 340 may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, the determination of the initial waveform based on the matching degree described elsewhere in the present disclosure (e.g., operation 608 illustrated in FIG. 6) may be obtained according to the process 700.

In 702, the processing device 120 (e.g., the waveform determination module 420) may identify a highest matching degree among multiple matching degrees between a pulse sequence and multiple candidate reference sequences. Each matching degree may be determined as described in connection with operation 606 in FIG. 6.

In some embodiments, the multiple candidate reference sequences may include two or more candidate reference sequences with the highest matching degree. That is, the matching degrees of the two or more candidate reference sequences may have the same value. In this regard, the processing device 120 may determine a reference sequence with the highest matching degree according to a hierarchy of priorities of the two or more candidate reference sequences. The processing device 120 may designate a candidate reference sequence of the highest matching degree with a higher hierarchy as the reference sequence. For instance, a feature directly corresponding to a tolerance parameter (or a patient or device safety issue) may have a higher priority than a feature corresponding to a focus parameter. Merely by way of example, for two candidate reference sequences with the highest matching degree, the processing device 120 may designate the candidate reference sequence whose similarity degree of the gradient amplitude is higher than the other as the reference sequence. The processing device 120 may designate the candidate reference waveform of the reference sequence as a reference waveform. In some embodiments, the hierarchy of priorities of candidate reference sequences may be a default setting of the MRI system 100 or preset by a user or operator via the terminal device 140. According to some embodiments of the present disclosure, when the processing device 120 determines that the multiple candidate reference sequences include two or more candidate reference sequences with the highest matching degree, the reference sequence may be determined according to a hierarchy of priorities, thereby preventing an MRI device from malfunctioning when an error occurs during a matching process.

In 704, the processing device 120 (e.g., the waveform determination module 420) may determine whether the pulse sequence matches a reference sequence of the highest matching degree. In response to determining that the pulse sequence matches the reference waveform of the highest matching degree, the processing device 120 may proceed to perform operation 706. In response to determining that the pulse sequence does not match the reference waveform of the highest matching degree, the processing device 120 may proceed to perform operation 708.

In some embodiments, when the highest matching degree between the pulse sequence and the reference sequence reaches a maximum value of the matching degree, the processing device 120 may determine that the pulse sequence matches the reference sequence. For example, a matching degree of 100% may indicate that the pulse sequence matches the reference sequence. As another example, for a grading system in which 10 is the highest grade allowed in the system, a matching degree of 10 may indicate that the pulse sequence matches the reference sequence. The pulse sequence matches the reference sequence may refer that each of one or more first features of the pulse sequence (or each of first features according to a matching rule described in connection with operation 606) may be the same as or equal to one of one or more second features of the reference sequence. That is, a first feature may be the same as the corresponding second feature.

In some embodiments, the processing device 120 may compare the highest matching degree with a matching degree threshold, such as 60%, 70%, 80%, 90%, etc. When the highest matching degree is greater than the matching degree threshold, the processing device 120 may determine that the pulse sequence matches the reference sequence. When the highest matching degree is less than the matching degree threshold, the processing device 120 may determine that the pulse sequence does not match the reference sequence.

In 706, the processing device 120 (e.g., the waveform determination module 420) may designate the reference waveform of the highest matching degree as an initial waveform corresponding to the pulse sequence.

In 708, the processing device 120 (e.g., the waveform determination module 420) may obtain one or more difference features between the one or more first features of the pulse sequence and the one or more second features of the reference sequence.

As used herein, a difference feature refers to a feature in which the pulse sequence is different from a reference sequence. For example, for a feature as the RF bandwidth, if the first RF bandwidth is 0.5 MHz and the second RF bandwidth is 1 MHz, the RF bandwidth may be determined as the difference feature. It should be understood, the difference features may be features that need to be adjusted for determining an initial waveform corresponding to the pulse sequence.

In some embodiments, if the processing device 120 determines that the first features and the second features match based on the matching rule, and it is determined that the highest matching degree is greater than a threshold, the processing device 120 may designate features not included in the matching rule as difference features between the pulse sequence and the reference sequence. For example, both the first features and the second features include a first portion of features (or first portion features), a second portion of features (or second portion features), a third portion of features (or third portion features), and a forth portion of features (or forth portion features). If the matching rule includes the first portion features and the third portion features, the difference features may be the second portion features and the forth portion features.

In some embodiments, in response to determining that the pulse sequence does not match the reference sequence, the processing device 120 may determine an initial waveform based on a relationship between the pulse sequence and the initial waveform to ensure that an MRI scan may not be interrupted so that the scanning process can proceed. As described in the present disclosure, although it may take a lot of time to directly obtain the initial waveform corresponding to the pulse sequence, however, if the initial waveform is not obtained after it is determined that the pulse sequence does not match the reference sequence, the MRI scan may be interrupted. If a reference waveform whose matching degree is less than the matching degree threshold is selected as the initial waveform, it may cause a poor quality of an obtained MR image.

In some embodiments, in response to determining that the pulse sequence does not match any reference sequence, the processing device 120 may identify one other candidate reference sequences whose matching degree(s) to the pulse sequence is/are higher than at least one other candidate reference sequences, and determine an initial waveform based on one or more reference waveforms corresponding to the identified one or more candidate reference sequences. For instance, the initial waveform may be determined based on one or more reference waveforms by interpolation or extrapolation. The interpolation or extrapolation may be performed with respect to one or more parameters of the one or more reference waveforms specified in the matching rule.

In 710, the processing device 120 (e.g., the waveform determination module 420) may determine the initial waveform by adjusting the reference waveform of the highest matching degree based on the one or more difference features.

The processing device 120 may adjust the second features as the corresponding first features based on the difference features. For example, if a difference feature between the first features of the pulse sequence and the second features of the reference sequence is the amplitude, the processing device 120 may adjust the second amplitude of the reference waveform as the first amplitude to obtain an updated reference waveform with the first amplitude. The processing device 120 may designate the updated reference waveform as the initial waveform corresponding to the pulse sequence.

In some embodiments, the processing device 120 may adjust the reference waveform based on one or more adjusting algorithm. The waveform adjusting algorithm may be a RF shimming algorithm which is used to improve B1 non-homogeneity. The RF shimming algorithm may include but not limited to algorithms that adjust waveform amplitude, waveform slope, waveform phase, waveform profile, etc.

It should be noted that, by adjusting the reference waveform corresponding to the reference sequence that does not match the pulse sequence to obtain the initial waveform corresponding to the pulse sequence, the effect on the quality of scanning using the MRI device based on an initial waveform determined by matching only feature(s) specified in the matching rule, instead of a more complete set of features of the pulse sequence, may be reduced and the scanning speed may be improved.

It should be noted that the above description regarding process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 708 and operation 710 may be combined into a single operation. As another example, one or more other optional operations (e.g., a storing operation) may be added elsewhere in the process 700.

FIG. 8 is a diagram illustrating an exemplary user interface associated with a tolerance parameter and/or a focus parameter according to some embodiments of the present disclosure. As shown in FIG. 8, the left end of the scale bar 810 may represent a minimum value of the tolerance parameter, and the right end of the scale bar 810 may represent a maximum value of the tolerance parameter. For example, the tolerance parameter may be an acoustic noise expectation (dB), a SAR (W/Kg), or a scanning time (min). The SAR may includes a whole body SAR, a partial body SAR, a local extremity SAR, a local trunk SAR or a head SAR, etc. A user or an operator may drag the adjustment bar 820 to specify a value of the tolerance parameter. The processing device 120 may determine a focus parameter based on the tolerance parameter. In some embodiments, for a same pulse sequence, the greater the tolerance parameter is, the less the focus parameter may be. For example, the minimum value of the acoustic noise expectation may correspond to a longest scanning time (e.g., 4 minutes), while the maximum value of the acoustic noise expectation may correspond to a shortest scanning time (e.g., 2.5 minutes). In some embodiments, the processing device 120 may display the focus parameter corresponding to the tolerance parameter specified by the user on the user interface 800. For example, if the tolerance parameter is the acoustic noise expectation (e.g., 20 dB), the focus parameter may be a scanning time (e.g., 4 minutes) determined by the processing device 120 based on the acoustic noise expectation. As another example, if the tolerance parameter is a maximum whole body SAR (e.g., 1.6 W/Kg at 3.0 Tesla), the focus parameter may be a scanning time (e.g., 4 minutes) determined based on the SAR. Through the user interface 800, the user may conveniently determine whether the tolerance parameter and/or the corresponding focus parameter are within an acceptable range, thereby improving the user experience.

Figure 9C:
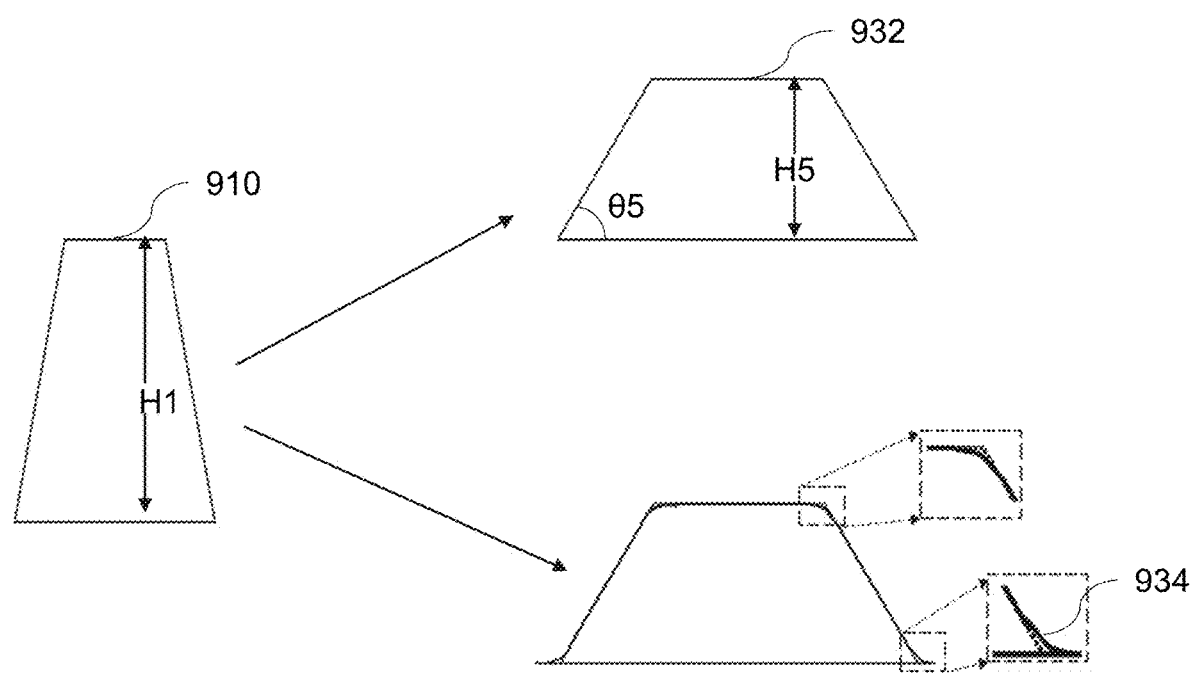
FIG. 9C is a schematic diagram illustrating an exemplary process for adjusting a gradient waveform for reducing a noise caused by gradient coils of an MRI device according to some embodiments of the present disclosure.

FIGS. 9A to 9C are schematic diagrams illustrating exemplary processes for adjusting a gradient waveform for reducing a noise caused by gradient coils of an MRI device according to some embodiments of the present disclosure. Generally, a high level of noise is primarily due to a current provided to gradient coils for spatial encoding and readout during an MRI process. The noise may be produced by vibrations in the gradient coils due to induced Lorentz forces which are associated with the gradient waveform applied on the gradient coils. The noises caused by the MRI device may be reduced by reducing the rising/falling slope and/or reducing the gradient field amplitude of the gradient waveform. Therefore, in order to reduce noises caused by the MRI device, the processing device 120 may adjust the gradient waveform applied to the gradient coils. For example, the processing device 120 may maintain the gradient field amplitude (or current amplitude applied to the gradient coils) and reduce the rising/falling slope of the gradient waveform. As another example, the area of the gradient waveform may remain constant, i.e., the zeroth moment of the gradient waveform may remain unchanged.

Specifically, when the noise is reduced while maintaining the gradient field amplitude of the gradient waveform, the processing device 120 may decrease a rising and/or falling slope of the gradient waveform. For example, for a pulse sequence that needs a high gradient field, the high gradient field may shorten the echo gap and speed up an acquisition rate of MR signals, thereby improving the signal-to-noise ratio (SNR) of the MR signals acquired using the MRI device. In this regard, the acoustic noise may be reduced by decreasing the rising/falling slope of the gradient waveform. As shown in FIG. 9A, waveform 910 represents a gradient waveform before being adjusted. Waveform 912 represents a gradient waveform after being adjusted by maintaining the gradient field amplitude (represented by letter H) of waveform 910, and decreasing a rising and/or falling slope of waveform 910. As described in the present disclosure, since a slope of a line is associated with a tilt angle of the line, the rising and/or falling slope of the gradient waveform may be represented by an angle between a waistline of the gradient waveform and the horizontal line (e.g., the rising slope of waveform 912 being represented by angle θ2 between straight line 914 and horizontal line 916). Accordingly, the rising and/or falling slope of waveforms 910 and 912 may be represented by symbols θ1 and θ2, wherein θ1>θ2. In some embodiments, the pulse sequence that needs a high gradient field may include an ultra-fast sequence or a diffusion-weighted imaging sequence, or the like, or any combination thereof. Exemplary ultra-fast sequences may include a single-shot rapid acquisition with relaxation enhancement (SS-RARE), a turbo gradient spin echo (Turbo-GRE), an echo planar, etc.

When the noise is reduced while maintaining the area of the gradient waveform, the processing device 120 may process the gradient waveform by decreasing the gradient field amplitude, decreasing a rising and/or falling slope, decreasing a gradient change rate of the gradient waveform, or the like. As shown in FIG. 9B, waveform 922 represents a waveform after being adjusted by maintaining the rising and falling slope of waveform 910 (represented by symbols θ1 and θ3, wherein θ1=θ3), and decreasing the gradient field amplitude (represented by letter H2, wherein H1>H2). Waveform 924 represents a waveform after being adjusted by maintaining the gradient field amplitude (represented by letter H3, wherein H1=H3), and decreasing the rising and falling slope of the waveform 910 (represented by symbols θ4, wherein θ1>θ4). Waveform 926 represents a waveform after being adjusted by maintaining the gradient field amplitude (represented by letter H3, wherein H1=H3), and decreasing the gradient change rate of the waveform 910. The areas of waveforms 922, 924, or 926 are equal to the area of waveform 910.

As shown in FIG. 9C, waveform 932 represents a waveform after being adjusted by decreasing both the gradient field amplitude (represented by letter H5, wherein H1>H5), and the rising and/or falling slope of waveform 910 (represented by symbols θ5, wherein θ1>θ5). Waveform 934 represents a waveform after being adjusted based on waveform 932, i.e., decreasing the gradient change rate of waveform 932. The area of waveforms 932 or 934 is equal to the area of waveform 910.

FIGS. 10A and 10B are schematic diagrams illustrating exemplary processes for adjusting a waveform according to some embodiments of the present disclosure. In some embodiments, noises produced by gradient coils of an MRI device may be reduced by adjusting a profile of a gradient waveform applied to the gradient coils. For example, the noises produced by the gradient coils may be reduced by using a curved waveform with the same area as the gradient waveform instead of directly using the gradient waveform (e.g., a waveform of phase encoding gradients). As shown in FIG. 10A, waveforms 1010, 1020, and 1030 represent different gradient waveforms before being adjusted. Waveforms 1012, 1022, and 1032 represent different adjusted waveforms by adjusting profiles of waveforms 1010, 1020, and 1030. An area of each of waveforms 1012, 1022, and 1032 may be the same as an area of the corresponding gradient waveform (i.e., waveforms 1010, 1020, or 1030).

In some embodiments, for a gradient waveform (e.g., a flow compensation gradient waveform) including a plurality of adjacent sub-waveforms with opposite gradient field amplitudes, the noises may be reduced by using a plurality of curved waveforms each of which corresponds to one adjacent sub-waveform. A total area of the curved waveforms may be the same as a total area of the adjacent sub-waveforms. As shown in FIG. 10B, waveforms 1040 and 1050 represent two adjacent sub-waveforms with opposite gradient field amplitudes before being adjusted. Waveforms 1042 and 1052 represent curved waveforms corresponding to waveforms 1040 and 1050. A total area of waveforms 1042 and 1052 may be the same as a total area of waveforms 1040 and 1050.

Figure 11:
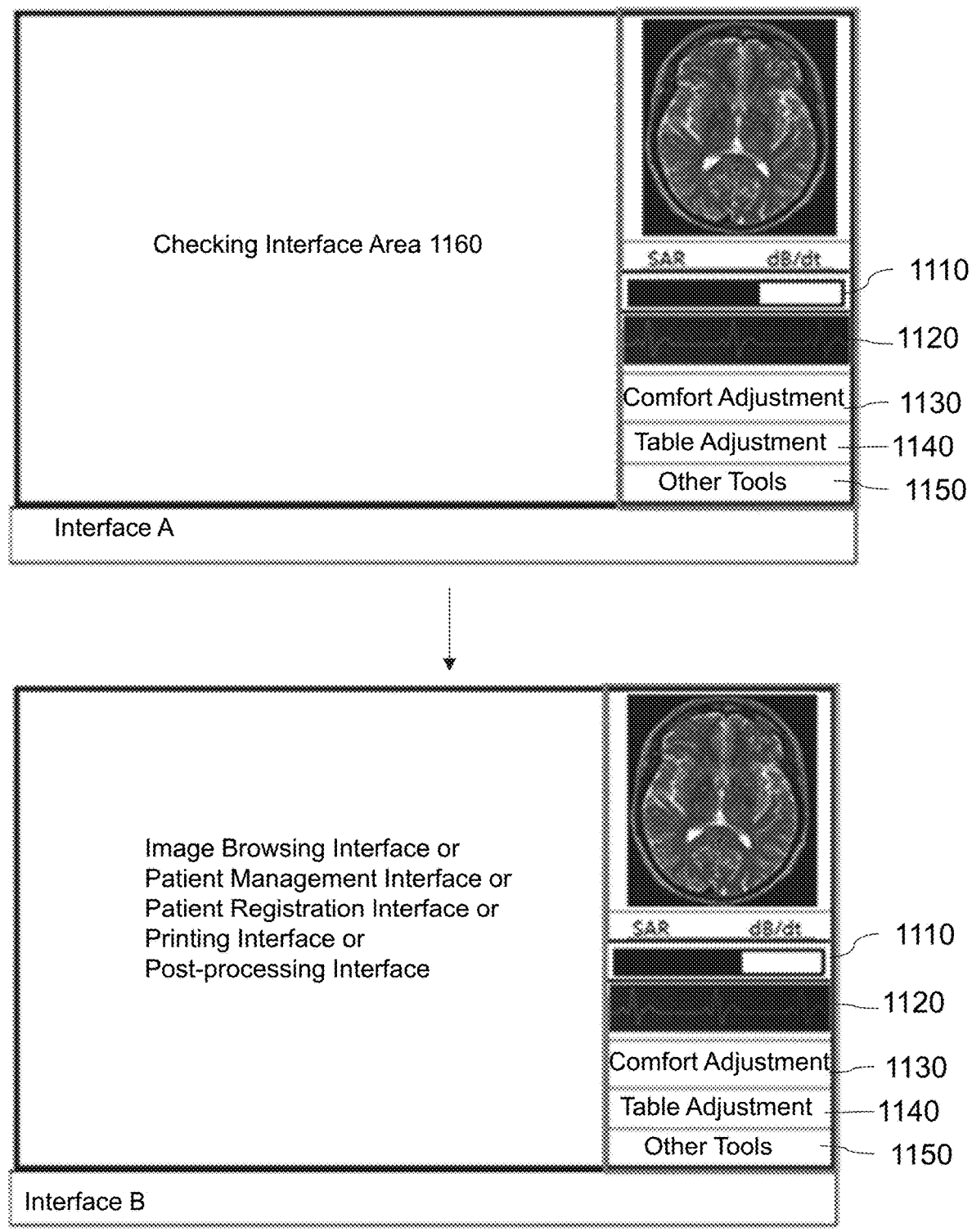
FIG. 11 is a schematic diagram illustrating an exemplary user interface according to some embodiments of the present disclosure.

FIG. 11 is a schematic diagram illustrating an exemplary user interface according to some embodiments of the present disclosure. The user interface may be displayed on a terminal device (e.g., the terminal device 140) in communication with a processing device (e.g., the processing device 120) of an MRI device. As shown in FIG. 11, the user interface may include a checking interface area 1160, a scan monitoring area, or the like, or a combination thereof. The scan monitoring area may include a SAR monitoring bar 1110, an electrocardiogram (ECG) monitoring area 1120, a comfort adjustment area 1130, a table adjustment area 1140, or other tools 1150. The SAR monitoring bar 1110 may be configured to monitor the absorption of RF energy by an object being imaged. The electrocardiogram (ECG) monitoring area 1120 may be configured to display the motion status of the object's heart. The comfort adjustment area 1130 may be configured to adjust a tolerance parameter. The table adjustment area 1140 may be configured to move the object (e.g., a patient) into or out of the scanning cavity of the MRI device, or to a center of a scanning area of the MRI device. In some embodiments, the user interface may be triggered by a user (e.g., a doctor) to switch from interface A to interface B for image browsing, patient management, patient registration, printing, post-processing, etc. In some embodiments, when the MRI device is not scanning an object, or when a relatively large interface is needed, the scan monitoring area may be hidden.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for magnetic resonance imaging (MRI), comprising:
   at least one non-transitory storage device storing executable instructions, and
   at least one processor in communication with the at least one non-transitory storage device, when executing the executable instructions, causing the system to perform operations including:
      obtaining a pulse sequence for scanning an object;
      determining, based on the pulse sequence, an initial waveform;

obtaining a tolerance parameter associated with the pulse sequence, wherein the tolerance parameter includes at least one of a scanning time, an acoustic noise expectation, or a specific absorption rate (SAR);

determining a target waveform for scanning the object by adjusting, based on the tolerance parameter, the initial waveform; and generating an image by causing an MRI device to scan the object based on the target waveform.

2. A magnetic resonance (MR) apparatus comprising:

an MR scanner including a gradient coil system;

a user interface configured to enable a user to input a tolerance parameter associated with a pulse sequence, wherein the tolerance parameter includes at least one of a scanning time, an acoustic noise expectation, or a specific absorption rate (SAR);

a processing device configured to determine an initial waveform; based on the pulse sequence and determine a target waveform for scanning an object by adjusting the initial waveform based on the tolerance parameter; and a control device configured to cause the MR scanner to generate an image by scanning the object according to the target waveform, wherein a gradient field corresponding to the target waveform is produced in the MR scanner by the gradient coil system of the MR scanner.

3. A method implemented on a computing device including at least one processor and at least one non-transitory storage medium, and a communication platform connected to a network, the method comprising:

obtaining a pulse sequence for scanning an object;

determining, based on the pulse sequence, an initial waveform;

obtaining a tolerance parameter associated with the pulse sequence, wherein the tolerance parameter includes at least one of a scanning time, an acoustic noise expectation, or a specific absorption rate (SAR);

determining a target waveform for scanning the object by adjusting, based on the tolerance parameter, the initial waveform; and generating an image by causing an MRI device to scan the object based on the target waveform.

4. The system of claim 1, wherein the pulse sequence includes at least one of a radiofrequency (RF) pulse sequence or a gradient pulse sequence.

5. The system of claim 1, wherein the determining a target waveform for scanning the object by adjusting, based on the tolerance parameter, the initial waveform includes:

determining the target waveform based on a relationship among the pulse sequence, the tolerance parameter, and the target waveform.

6. The system of claim 1, wherein the determining a target waveform for scanning the object by adjusting, based on the tolerance parameter, the initial waveform includes:

querying a waveform database based on the pulse sequence and the tolerance parameter; and determining the target waveform based on a query result.

7. The system of claim 1, wherein the determining, based on the pulse sequence, an initial waveform includes:

determining the initial waveform based on a relationship between the pulse sequence and the initial waveform.

8. The system of claim 1, wherein the determining, based on the pulse sequence, an initial waveform includes:

obtaining one or more first features of the pulse sequence, the one or more first features corresponding to the initial waveform;

obtaining one or more second features of each of multiple candidate reference sequences from a waveform library;

determining, based on the one or more first features and the one or more second features, a matching degree between the pulse sequence and each of the multiple candidate reference sequences; and determining, based on the matching degree, the initial waveform.

9. The system of claim 8, wherein the determining, based on the matching degree, the initial waveform includes:

identifying a highest matching degree among the matching degrees between the pulse sequence and the multiple candidate reference sequences; and determining, based on a reference waveform corresponding to the reference sequence of the highest matching degree, the initial waveform.

10. The system of claim 1, wherein the adjusting, based on the tolerance parameter, the initial waveform includes:

adjusting one or more waveform parameters of the initial waveform based on the tolerance parameter, wherein the one or more waveform parameters of the initial waveform includes at least one of a pulse amplitude, a pulse phase, a slope, or a profile of the initial waveform.

11. The system of claim 4, wherein the tolerance parameter includes the acoustic noise expectation corresponding to the gradient pulse sequence, and the at least one processor is further configured to cause the system to perform additional operations including:

determining an estimated scanning time for scanning the object based on the target waveform;

determining whether the estimated scanning time satisfies a compliance condition; and in response to determining that the estimated scanning time fails to satisfy the compliance condition, adjusting the acoustic noise expectation corresponding to the gradient pulse sequence.

12. The system of claim 4, wherein the tolerance parameter includes the scanning time corresponding to the gradient pulse sequence, and the at least one processor is further configured to cause the system to perform additional operations including:

determining an estimated acoustic noise corresponding to the gradient pulse sequence based on the target waveform;

determining whether the estimated acoustic noise corresponding to the gradient pulse sequence satisfies a compliance condition; and in response to determining that the estimated acoustic noise corresponding to the gradient pulse sequence fails to satisfy the compliance condition, adjusting the scanning time corresponding to the gradient pulse sequence.

13. The system of claim 11, wherein the target waveform includes at least one gradient waveform, wherein the causing the MRI device to scan the object based on the target waveform includes:

initiating a gradient channel of the MRI device corresponding to the at least one gradient waveform, the gradient channel including at least one of an X-axis gradient channel, a Y-axis gradient channel, or a Z-axis gradient channel; and transmitting the at least one gradient waveform using the corresponding gradient channel.

14. The system of claim 4, wherein the tolerance parameter includes the specific absorption rate (SAR) corresponding to the RF pulse sequence, and the at least one processor is further configured to cause the system to perform additional operations including:
- determining an estimated scanning time for scanning the object based on the target waveform;
- determining whether the estimated scanning time satisfies a compliance condition; and
- in response to determining that the estimated scanning time fails to satisfy the compliance condition, adjusting the SAR.

15. The system of claim 4, wherein the tolerance parameter includes the scanning time corresponding to the RF pulse sequence, and the at least one processor is further configured to cause the system to perform additional operations including:
- determining an estimated SAR corresponding to the RF pulse sequence based on the target waveform;
- determining whether the estimated SAR corresponding to the RF pulse sequence satisfies a compliance condition; and
- in response to determining that the estimated SAR corresponding to the RF pulse sequence fails to satisfy the compliance condition, adjusting the scanning time corresponding to the RF pulse sequence.

16. The system of claim 1, wherein the target waveform includes at least one RF pulse waveform, wherein the causing the MRI device to scan the object based on the target waveform includes:
- performing a pulse frequency modulation on the at least one RF pulse waveform;
- initiating an RF transmission channel of the MRI device corresponding to the at least one RF pulse waveform; and
- transmitting the at least one RF pulse waveform using the corresponding RF transmission channel simultaneously.

17. The system of claim 1, wherein the generating an image by causing an MRI device to scan the object based on the target waveform includes:
- obtaining an MRI signal of the object based on the target waveform; and
- generating the image of the object by reconstructing the MRI signal;

the at least one processor is further configured to cause the system to perform the operations including:
- determining whether the image meets a quality threshold; and
- in response to determining that the image does not meet the quality threshold, adjusting the tolerance parameter.

18. The MR apparatus of claim 2, wherein the tolerance parameter includes the acoustic noise expectation corresponding to the pulse sequence, the control device is further configured to:
- determine an estimated scanning time for scanning the object based on the target waveform;
- determine whether the estimated scanning time satisfies a compliance condition; and
- in response to determining that the estimated scanning time fails to satisfy the compliance condition, adjust the acoustic noise expectation corresponding to the pulse sequence.

19. The MR apparatus of claim 2, wherein the user interface includes at least one of a SAR monitoring bar, an electrocardiogram (ECG) monitoring area, or a comfort adjustment area.

20. The system of claim 2, wherein the user interface includes a scale bar configured to allow the user to specify a value of the tolerance parameter by dragging the scale bar.

* * * * *